(12) United States Patent
Boléa et al.

(10) Patent No.: US 8,697,744 B2
(45) Date of Patent: Apr. 15, 2014

(54) SUBSTITUTED 5,6-DIHYDRO-4H-THIAZOLO[4,5-E]INDAZOLES AND THEIR USE AS POSITIVE ALLOSTERIC MODULATORS OF METABOTROPIC GLUTAMATE RECEPTORS

(75) Inventors: Christelle Boléa, Geneva (CH); Sylvain Celanire, Geneva (CH)

(73) Assignee: Addex Pharma S.A., Geneva (CH)

( * ) Notice: Subject to any disclaimer, the term of this patent is extended or adjusted under 35 U.S.C. 154(b) by 16 days.

(21) Appl. No.: 12/998,955

(22) PCT Filed: Jan. 12, 2010

(86) PCT No.: PCT/EP2010/050304
§ 371 (c)(1),
(2), (4) Date: Jun. 18, 2011

(87) PCT Pub. No.: WO2010/079238
PCT Pub. Date: Jul. 15, 2010

(65) Prior Publication Data
US 2011/0319425 A1 Dec. 29, 2011

(30) Foreign Application Priority Data
Jan. 12, 2009 (GB) .................................. 0900404.5

(51) Int. Cl.
*A61K 31/30* (2006.01)
(52) U.S. Cl.
USPC ........... 514/443; 544/333; 544/405; 546/304; 548/359.5; 548/373.1
(58) Field of Classification Search
USPC .................. 514/443; 544/333, 405; 546/304; 548/359.5, 373.1
See application file for complete search history.

(56) References Cited

FOREIGN PATENT DOCUMENTS

| WO | WO-97/05137 A1 | 2/1997 |
|---|---|---|
| WO | WO-2005/007096 A2 | 1/2005 |
| WO | WO-2006/040279 A1 | 4/2006 |
| WO | WO-2007/032854 A1 | 3/2007 |
| WO | WO-2009/010455 A2 | 1/2009 |
| WO | WO-2009/070871 A1 | 6/2009 |

OTHER PUBLICATIONS

Zheng, G.Z., et. al., Structure-Activity Relationship of Triazafluorenone . . . , Journal of Medicinal Chemistry, 2005, vol. 48, pp. 7374-7388, American Chemical Society.
Stachowicz, K., et al., Anxiolytic-like effects of PHCCC, an allosteric modulator of mGlu4 . . . , European Journal of Pharmacology, 2004, vol. 498, pp. 153-156, Elsevier B.V.
Tatarczynska, E., et al., Anxiolytic- and Antidepressant-Like Effects of Group III . . . , Polish Journal of Pharmacol., 2002, vol. 54(6), pp. 707-710, Institute of Pharmacology.
Toyono, T., et al., Expression of the Metabotropic Glutamate Receptor, mGluR4A, in the Taste Hairs of Taste Buds in Rat . . . , Arch. Histol. Cytol., 2002, vol. 65(1), pp. 91-96.
Uehara, S., et al., Metabotropic Glutamate Receptor Type 4 Is Involved in Autoinhibitory Cascade . . . , Diabetes, 2004, vol. 53, pp. 998-1006, American Diabetes Association.
Valenti, O., et al., Group III Metabotropic Glutamate Receptor-Mediated Modulation . . . , Journal of Neuroscience, 2003, vol. 23(18), pp. 7218-7226, Society for Neuroscience.
Valenti, O., et al., Group III Metabotropic . . . , Journal of Pharmacol. & Experim. Therapeutics, 2005, vol. 313(3), pp. 1296-1304, Amer. Soc. for Pharmacol.& Experim. Ther.,USA.
Vernon, A., et al., Neuroprotective Effects of Metabotropic . . . , European Journal of Neuroscience, 2005, vol. 22, pp. 1799-1806, Federation of European Neuroscience Societies.
Williams, R., et al., Positive Allosteric Modulators of the Metabotropic Glutamate . . . , Bioorganic & Medicinal Chemistry Letters, 2009, vol. 19, pp. 962-966, Elsevier Ltd.
Wilson, J., et al., Identification of Novel Positive Allosteric Modulators of mGlu8 Receptor, Neuropharmacology, 2005, vol. 49, p. 278.
Young, R., et al., Anatomy and Function of Group III Metabotropic Glutamate Receptors in Gastric Vagal Pathways, Neuropharmacology, 2008, vol. 54, pp. 965-975, Elsevier Ltd.
Kew, J., Positive and Negative Allosteric Modulation of Metabotropic Glutamate Receptors . . . , Pharmacology & Therapeutics, 2004, vol. 104(3), pp. 233-244, Elsevier Inc.
Knoflach, F., et al., Positive Allosteric Modulators of Metabotropic Glutamate 1 Receptor . . . , Proc. Natl. Acad. Sci. USA, 2001, vol. 98(23), pp. 13402-13407.
Konieczny, J., et al., The Influence of Group III Metabotropic Glutamate Receptor Stimulation by . . . , Neuroscience, 2007, vol. 145, pp. 611-620, Elsevier Ltd.
Lopez, S., et al., Targeting Group III Metabotropic Glutamate Receptors Produces . . . , Journal of Neuroscience, 2007, vol. 27(25), pp. 6701-6711, Society for Neuroscience.
Maj, M., et al., (–)-PHCCC a Positive Allosteric Modulator of mGluR4: Characterization, Mechanism of Action . . . , (Continued)

*Primary Examiner* — Douglas M Willis
(74) *Attorney, Agent, or Firm* — Law Offices of Gerard Bilotto, P.C.; Gerard Bilotto

(57) ABSTRACT

The present invention relates to novel compounds of Formula (I), wherein $X^1$, $X^2$, Y, $Z^1$, $Z^2$, $Z^3$, M and $(A)_m$ are defined as in Formula (I); invention compounds are modulators of metabotropic glutamate receptors—subtype 4 ("mGluR4") which are useful for the treatment or prevention of central nervous system disorders as well as other disorders modulated by mGluR4 receptors. The invention is also directed to pharmaceutical compositions and the use of such compounds in the manufacture of medicaments, as well as to the use of such compounds for the prevention and treatment of such diseases in which mGluR4 is involved.

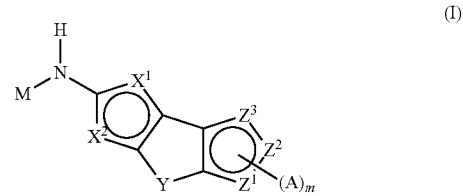

(I)

12 Claims, No Drawings

(56) References Cited

OTHER PUBLICATIONS

Neuropharmacology, 2003, vol. 45, pp. 895-906, Elsevier Ltd.

Marino, M., et al., Localization and Physiological Roles of Metabotropic Glutamate Receptors in the Direct and Indirect . . . , Amino Acids, 2002, vol. 23, pp. 185-191, Austria.

Marino, M., et al., Targeting the Metabotropic Glutamate Receptor . . . , Current Topics in Medicinal Chemistry, 2005, vol. 5(9), pp. 885-895, Bentham Science Publishers, Ltd.

Marino, M., et al., Allosteric Modulation of Group III Metabotropic Glutamate Receptor 4: A Potential . . . , Proc. Natl. Acad. Sci. USA, 2003, vol. 100(23), pp. 13668-13673.

Mathiesen, J., et al., Positive Allosteric Modulation of the Human Metabotropic . . . , British Journal of Pharmacology, 2003, vol. 138(6), pp. 1026-1030, Nature Publishing Group.

Millan, C., et al., Subtype-specific Expression of Group . . . , Journal of Biological Chemistry, 2002, vol. 277(49), pp. 47796-47803, American Soc. Biochem. & Molec. Biology Inc.

Mitsukawa, K., et al., A Selective Metabotropic Glutamate Receptor 7 Agonist: Activation of Receptor . . . , Proc. Natl. Acad. Sci. USA, 2005, vol. 102(51), pp. 18712-18717.

Monastyrskaia, K., et al., Effect of the Umami Peptides on the Ligand Binding and Function . . . , British Journal of Pharmacology, 1999, vol. 128, pp. 1027-1034, Stockton Press.

Mutel, V., Therapeutic Potential of Non-Competitive, Subtype-Selective Metabotropic . . . , Expert Opinion Ther. Patents, 2002, vol. 12(12), pp. 1-8, Ashley Publications Ltd.

Nakanishi, S., et al., Glutamate Receptors: Brain Function and Signal Transduction, Brain Research Reviews, 1998, vol. 26, pp. 230-235, Elsevier Science B.V.

Niswender, C., et al., Positive Allosteric Modulators of the Metabotropic Glutamate . . . , Bioorganic & Medicinal Chemistry Letters, 2008, vol. 18, pp. 5626-5630, Elsevier Ltd.

Niswender, C., et al., Discovery, Characterization, and . . . , Molecular Pharmacology, 2008, vol. 74(5), pp. 1345-1358, Amer. Soc. For Pharmacology & Experim. Therapeutics, USA.

O'Brien, J., et al., A Family of Highly Selective Allosteric . . . , Molecular Pharmacology, 2003, vol. 64(3), pp. 731-740, Amer.Soc. For Pharmacology & Experim.Therapeutics, USA.

Page, A., et al., Metabotropic Glutamate Receptors Inhibit Mechanosensitivity in Vagal . . . , Gastroenterology, 2005, vol. 128, pp. 402-410, American Gastroenterological Assoc.

Ritzen, A., et al., Molecular Pharmacology and Therapeutic Prospects . . . , Basic & Clinical Pharmacol. & Toxicol., 2005, vol. 97, pp. 202-213, Pharmacology & Toxicology,Denmark.

Schoepp, D., et al., Pharmacological Agents Acting at Subtypes of Metabotropic Glutamate Receptors, Neuropharmacology, 1999, vol. 38, pp. 1431-1476, Elsevier Science Ltd.

Battaglia, G., et al., Pharmacological Activation of mGlu4 Metabotropic Glutamate Receptors Reduces . . . , Jornal of Neuroscience, 2006, vol. 26(27), pp. 7222-7229.

Besong, G., et al., Activation of Group III Metabotropic Glutamate Receptors Inhibits the Production of RANTES . . . , Journal of Neuroscience, 2002, vol. 22(13), pp. 5403-5411.

Bradley, S., et al., Immunohistochemical Localization of Subtype 4a Metabotropic Glutamate Receptors . . . , Journal of Comparative Neurology, 1999, vol. 407, pp. 33-46.

Bruno, V., et al., Selective Activation of mGlu4 Metabotropic Glutamate Receptors is Protective . . . , Journal of Neuroscience, 2000, vol. 20(17), pp. 6413-6420.

Conn, P.J., et al., Metabotropic Glutamate Receptors in the Basal Ganglia Motor Circuit, Nature Review Neuroscience, 2005, vol. 6, pp. 787-798, Nature Publishing Group.

Corti, C., et al., Distribution and Synaptic Localisation of the Metabotropic Glutamate . . . , Neuroscience, 2002, vol. 110(3), pp. 403-420, Elsevier Science Ltd, Great Britain.

Engers, D., et al, Synthesis and Evaluation of a Series of Heterobiarylamides . . . , Journal of Medicinal Chemistry, 2009, vol. 52(14), pp. 4115-4118, American Chemical Society.

Johnson, M.P., et al., Modulation of Stress-Induced and Stimulated Hyperprolactinemia with the Group . . . , Neuropharmacology, 2002, vol. 43, pp. 799-808, Elsevier Science Ltd.

Johnson, M.P., et al., Discovery of Allosteric Potentiators . . . , Journal of Medicinal Chemistry, 2003, vol. 46(15), pp. 3189-3192, American Chemical Society.

Johnson, M.P., et al., Allosteric Modulators of Metabotropic Glutamate Receptors . . . , Biochemical Society Transactions, 2004, vol. 32(5), pp. 881-887, Biochemical Society.

SUBSTITUTED 5,6-DIHYDRO-4H-THIAZOLO[4,5-E]INDAZOLES AND THEIR USE AS POSITIVE ALLOSTERIC MODULATORS OF METABOTROPIC GLUTAMATE RECEPTORS

This application is a national stage application under 35 U.S.C, §371 of PCT/EP2020/059034, filed on Jan. 12, 2010, which claims benefit under 35 U.S.C. §119(a-d) and 365(b) from UK patent application GB0900404.5, filed on Jan. 12, 2009.

SUMMARY OF THE INVENTION

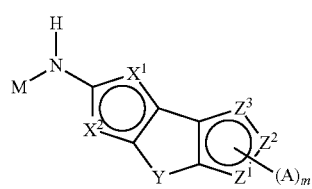

The present invention relates to novel compounds of Formula (I), wherein $X^1$, $X^2$, Y, $Z^1$, $Z^2$, $Z^3$, M and $(A)_m$ are defined as in Formula (I); invention compounds are modulators of metabotropic glutamate receptors—subtype 4 ("mGluR4") which are useful for the treatment or prevention of central nervous system disorders as well as other disorders modulated by mGluR4 receptors. The invention is also directed to pharmaceutical compositions and the use of such compounds in the manufacture of medicaments, as well as to the use of such compounds for the prevention and treatment of such diseases in which mGluR4 is involved.

BACKGROUND OF THE INVENTION

Glutamate is the major amino-acid transmitter in the mammalian central nervous system (CNS). Glutamate plays a major role in numerous physiological functions, such as learning and memory but also sensory perception, development of synaptic plasticity, motor control, respiration and regulation of cardiovascular function. Furthermore, glutamate is at the center of several different neurological and psychiatric diseases, where there is an imbalance in glutamatergic neurotransmission.

Glutamate mediates synaptic neurotransmission through the activation of ionotropic glutamate receptor channels (iGluRs), namely the NMDA, AMPA and kainate receptors which are responsible for fast excitatory transmission (Nakanishi et al., (1998) Brain Res. Rev., 26:230-235).

In addition, glutamate activates metabotropic glutamate receptors (mGluRs) which have a more modulatory role that contributes to the fine-tuning of synaptic efficacy.

The mGluRs are G protein-coupled receptors (GPCRs) with seven-transmembrane spanning domains and belong to GPCR family 3 along with the calcium-sensing, GABAb and pheromone receptors.

The mGluR family is composed of eight members. They are classified into three groups (group I comprising mGluR1 and mGluR5; group II comprising mGluR2 and mGluR3; group III comprising mGluR4, mGluR6, mGluR7 and mGluR8) according to sequence homology, pharmacological profile and nature of intracellular signalling cascades activated (Schoepp et al., (1999) Neuropharmacology, 38:1431-1476).

Glutamate activates the mGluRs through binding to the large extracellular amino-terminal domain of the receptor, herein called the orthosteric binding site. This activation induces a conformational change of the receptor which results in the activation of the G-protein and intracellular signalling pathways.

In the central nervous system, mGluR4 receptors are expressed most intensely in the cerebellar cortex, basal ganglia, sensory relay nuclei of the thalamus and hippocampus (Bradley et al., (1999) Journal of Comparative Neurology, 407:33-46; Corti et al., (2002) Neuroscience, 110:403-420). The mGluR4 subtype is negatively coupled to adenylate cyclase via activation of the Gαi/o protein, is expressed primarily on presynaptic terminals, functioning as an autoreceptor or heteroceptor and activation of mGluR4 leads to decreases in transmitter release from presynaptic terminals (Corti et al., (2002) Neuroscience, 110:403-420; Millan et al., (2002) Journal of Biological Chemistry, 277:47796-47803; Valenti et al., (2003) Journal of Neuroscience, 23:7218-7226).

Orthosteric agonists of mGluR4 are not selective and activate the other Group III mGluRs (Schoepp et al., (1999) Neuropharmacology, 38:1431-1476). The Group III orthosteric agonist L-AP4 was able to reduce motor deficits in animal models of Parkinson's disease (Valenti et al., (2003) J. Neurosci., 23:7218-7226) and decrease excitotoxicity (Bruno et al., (2000) J. Neurosci., 20; 6413-6420) and these effects appear to be mediated through mGluR4 (Marino et al., (2005) Curr. Topics Med. Chem., 5:885-895). In addition to LAP-4, ACPT-1, another selective group III mGluR agonist has been shown to caused a dose-and-structure dependant decrease in haloperidol-induced catalepsy and attenuated haloperidol-increased Proenkephalin mRNA expression in the striatum (Konieczny et al., (2007) Neuroscience, 145: 611-620). Furthemore, Lopez et al. (2007, J. Neuroscience, 27:6701-6711) have shown that bilateral infusions of ACPT-I or LAP-4 into the globus pallidus fully reversed the severe akinetic deficits produced by 6-hydroxydopamine lesions of nigrostriatal dopamine neurons in a reaction-time task without affecting the performance of controls. In addition, the reversal of haloperidol-induced catalepsy by intrapallidal ACPT-1 was prevented by concomitant administration of a selective group III receptor antagonist (RS)-alpha-cyclopropyl-4-phosphonophenylglycine. The opposite effects produced by group III mGluR activation in the SNr strongly suggest a role of mGluR4 rather than others mGluR receptor sub-types in normalizing basal ganglia activity (Lopez et al. 2007).

These results suggest that, among mGluRs subtypes, mGluR4 is believed to be the most interesting novel drug target for the treatment of Parkinson's disease (for a review see Conn et al., (2005) Nature Review Neuroscience, 6:787-798).

Symptoms of Parkinson's disease appear to be due to an imbalance in the direct and indirect output pathways of the basal ganglia and reduction of transmission at the inhibitory GABAergic striato-pallidal synapse in the indirect pathway may result in alleviation of these symptoms (Marino et al., (2002) Amino Acids, 23:185-191).

mGluR4 is more abundant in striato-pallidal synapses than in striato-nigral synapses, and its localization suggests function as a presynaptic heteroreceptor on GABAergic neurons (Bradley et al., (1999) Journal of Comparative Neurology, 407:33-46) suggesting that selective activation or positive modulation of mGluR4 would decrease GABA release in this synapse thereby decreasing output of the indirect pathway and reducing or eliminating the Parkinson's disease symptoms. Classical treatment of Parkinsonism typically involves the use of levodopa combined with carbidopa (SINEMET™) or benserazide (MADOPAR™). Dopamine agonists such as bromocriptine (PARLODEL™), lisuride and pergolide (CELANCE™) act directly on dopamine receptors and are also used for the treatment of Parkinsonism. These molecules have the same side-effect profile as levodopa.

A new avenue for developing selective compounds acting at mGluRs is to identify molecules that act through allosteric mechanisms, modulating the receptor by binding to a site different from the highly conserved orthosteric binding site.

Positive allosteric modulators of mGluRs have emerged recently as novel pharmacological entities offering this attractive alternative. This type of molecule has been discovered for mGluR1, mGluR2, mGluR4, mGluR5, mGluR7 and mGluR8 (Knoflach F. et al. (2001) Proc. Natl. Acad. Sci. USA, 98:13402-13407; Johnson M. P. et al., (2002) Neuropharmacology, 43:799-808; O'Brien J. A. et al., (2003) Mol. Pharmacol., 64:731-740; Johnson M. P. et al., (2003) J. Med. Chem., 46:3189-3192; Marino M. J. et al., (2003) Proc. Natl. Acad. Sci. USA, 100:13668-13673; Mitsukawa K. et al., (2005) Proc. Natl. Acad. Sci. USA, 102(51):18712-18717; Wilson J. et al., (2005) Neuropharmacology, 49:278; for a review see Mutel V., (2002) Expert Opin. Ther. Patents, 12:1-8; Kew J. N., (2004) Pharmacol. Ther., 104(3):233-244; Johnson M. P. et al., (2004) Biochem. Soc. Trans., 32:881-887; recently Ritzen A., Mathiesen, J. M. and Thomsen C., (2005) Basic Clin. Pharmacol. Toxicol., 97:202-213).

In particular molecules have been described as mGluR4 positive allosteric modulators (Maj et al., (2003) Neuropharmacology, 45:895-906; Mathiesen et al., (2003) British Journal of Pharmacology, 138:1026-1030). It has been demonstrated that such molecules have been characterized in in vitro systems as well as in rat brain slices where they potentiated the effect of LAP-4 in inhibiting transmission at the striato-pallidal synapse. These compounds do not activate the receptor by themselves (Marino et al., (2003) Proc. Nat. Acad. Sci. USA, 100:13668-13673). Rather, they enable the receptor to produce a maximal response to a concentration of glutamate or the Group III orthosteric agonist L-AP4 which by itself induces a minimal response.

PHCCC, a positive allosteric modulator of mGluR4 not active on other mGluRs (Maj et al., (2003) Neuropharmacology, 45:895-906), has been shown to be efficacious in animal models of Parkinson's disease thus representing a potential novel therapeutic approach for Parkinson's disease as well as for other motor disorders and disturbances (Marino et al., (2003) Proc. Nat. Acad. Sci. USA, 100:13668-13673), neurodegeneration in Parkinson's disease (Marino et al., (2005) Curr. Topics Med. Chem., 5:885-895; Valenti et al., (2005) J. Pharmacol. Exp. Ther., 313:1296-1304; Vernon et al., (2005) Eur. J. Neurosci., 22:1799-1806, Battaglia et al., (2006) J. Neurosci., 26:7222-7229), and neurodegeneration in Alzheimer's disease or due to ischemic or traumatic insult (Maj et al., (2003) Neuropharmacology, 45:895-906).

PHCCC also has been shown to be active in animal model of anxiety (Stachowicz et al., (2004) Eur. J. Pharmacol., 498:153-156). Previously, ACPT-1 has been showed to produce a dose-dependent anti-conflict effect after intrahippocampal administration and anti-depressant-like effects in rats after intracerebroventricular administration (Tatarczynska et al., (2002) Pol. J. Pharmacol., 54(6):707-710).

Activation of mGluR4 receptors which are expressed in α- and F-cells in the islets of Langerhans inhibits glucagon secretion. Molecules which activate or potentiate agonist activity of these receptors may be an effective treatment for hyperglycemia, one of the symptoms of type 2 diabetes (Uehara et al., (2004) Diabetes, 53:998-1006).

The β-chemokine RANTES is importantly involved in neuronal inflammation and has been implicated in the pathophysiology of multiple sclerosis. Activation of Group III mGluRs with L-AP4 reduced the synthesis and release RANTES in wild-type cultured astrocytes, whereas the ability of L-AP4 to inhibit RANTES was greatly decreased in astrocyte cultures from mGluR4 knockout mice (Besong et al., (2002) Journal of Neuroscience, 22:5403-5411). These data suggest that positive allosteric modulators of mGluR4 may be an effective treatment for neuroinflammatory disorders of the central nervous system, including multiple sclerosis and related disorders.

Two different variants of the mGluR4 receptor are expressed in taste tissues and may function as receptors for the umami taste sensation (Monastyrskaia et al., (1999) Br. J. Pharmacol., 128:1027-1034; Toyono et al., (2002) Arch. Histol. Cytol., 65:91-96). Thus positive allosteric modulators of mGluR4 may be useful as taste agents, flavour agents, flavour enhancing agents or food additives.

There are anatomical evidence that the majority of vagal afferents innervating gastric muscle express group III mGluRs (mGluR4, mGluR6, mGluR7 and mGluR8) and actively transport receptors to their peripheral endings (Page et al., (2005) Gastroenterology, 128:402-10). Recently, it was shown that the activation of peripheral group III mGluRs inhibited vagal afferents mechanosensitivity in vitro which translates into reduced triggering of transient lower oesophagal sphincter relaxations and gastroesophageal reflux in vivo (Young et al., (2008) Neuropharmacol, 54:965-975). Labelling for mGluR4 and mGluR8 was abundant in gastric vagal afferents in the nodose ganglion, at their termination sites in the nucleus tractus solitarius and in gastric vagal motoneurons. These data suggest that positive allosteric modulators of mGluR4 may be an effective treatment for gastro-esophageal reflux disease (GERD) and lower esophageal disorders and gastro-intestinal disorders.

International patent publication WO2005/007096 describes mGluR4 receptor positive allosteric modulator useful, alone or in combination with a neuroleptic agent, for treating or preventing movement disorders. However, none of the specifically disclosed compounds are structurally related to the compounds of the invention.

More recently, new mGluR4 receptor positive allosteric modulators have been described: pyrazolo[3,4-d]pyrimidine derivatives (Niswender et al., (2008) Bioorganic & Medicinal Chemistry Letters, 18(20):5626-5630), functionalized benzylidene hydrazinyl-3-methylquinazo line and bis-2,3-dihydroquinazolin-4(1H)-one (Williams et al., (2009) Bioorganic & Medicinal Chemistry Letters, 19:962-966) and heterobiarylamides (Engers et al, (2009) Journal of Medicinal Chemistry, 52 (14), 4115-4118). Niswender et al., described (±)-cis-2-(3,5-dichlorophenylcarbamoyl)cyclohexane carboxylic acid ((2008) Molecular Pharmacology, 74(5): 1345-1358), as a positive allosteric modulator of mGluR4 also having agonist activity. This moderately active molecule has demonstrated evidence of efficacy following icy injection in rat models of Parkinson's disease. International patent publications WO2009/070871 and WO2009/010455 have mentioned amido derivatives and novel heteroaromatic derivatives, respectively, as positive allosteric modulators of metabotropic glutamate receptors.

International patent publication WO2006/040279 describes (3-methanesulfonyl-phenyl)-(1-phenyl-4,5-dihydro-1H-pyrazolo[3',4':3,4]benzo[1,2-c]thiazol-7-yl)-amine, known to be a PI3 kinase modulator. This prior art compound is not included within the scope of the present invention, by virtue of the definition of $X^2$ in the claims ($X^2$ cannot be N).

The present inventors have discovered novel thiazole compounds of general Formula (I) which surprisingly show potent activity and selectivity on mGluR4 receptor. The compounds of the invention demonstrate advantageous properties over compounds of the prior art. Improvements have been observed in one or more of the following characteristics of the compounds of the invention: the potency on the target, the selectivity for the target, the bioavailability, the brain penetration, and the activity in behavioural models.

The present invention relates to a method of treating or preventing a condition in a mammal, including a human, the treatment or prevention of which is affected or facilitated by the neuromodulatory effect of mGluR4 modulators. In the case of the treatment of movement disorders such as Parkinson's disease, the compounds of the invention can be used alone or in combination with an agent selected from the group consisting of: levodopa, levodopa with a selective extracerebral decarboxylase inhibitor, carbidopa, entacapone, a COMT inhibitor or a dopamine agonist.

DETAILED DESCRIPTION OF THE INVENTION

The invention relates to compounds having metabotropic glutamate receptor 4 modulator activity. In its most general compound aspect, the present invention provides a compound according to Formula (I),

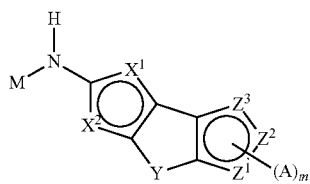

(I)

a pharmaceutically acceptable acid or base addition salt thereof, a stereochemically isomeric form thereof and an N-oxide form thereof, wherein:

M is selected from an optionally substituted 3 to 10 membered ring selected from the group of aryl, heteroaryl, heterocyclic and cycloalkyl;

$X^1$ is selected from the group of N, $NR^1$ and $CR^1$;

$X^2$ is selected from the group of S and $R^2C=CR^3$;

Y is selected from the group of $-CR^4R^5-CR^6R^7-$, $-CR^4R^5-CR^6R^7-CR^8R^9-$, $-C=O-CR^4R^5-CR^6R^7-$, $-O-CR^4R^5-$, $-O-CR^4R^5-CR^6R^7-$, $-NR^4-CR^5R^6-$, $-NR^4-CR^5R^6-CR^7R^8-$, $-S-CR^4R^5-$, $-S-CR^4R^5-CR^6R^7-$, $-SO-CR^4R^5-$, $-SO-CR^4R^5-CR^6R^7-$, $-SO_2-CR^4R^5-$ and $-SO_2-CR^4R^5-CR^6R^7-$;

$Z^1$, $Z^2$ and $Z^3$ are each independently selected from the group of N and C representing a 5 membered heteroaryl ring with a maximum of 2 N which may further be substituted by 1 to 2 radicals $(A)_m$;

m is an integer ranging from 1 to 2;

$(A)_m$ radicals are each independently selected from the group of hydrogen, halogen, $-CN$, $-OH$, $-CF_3$, $-SH$, $-NH_2$ and an optionally substituted radical selected from the group of $-(C_1-C_6)$alkyl, $-(C_1-C_6)$haloalkyl, $-(C_2-C_6)$alkynyl, $-(C_2-C_6)$alkenyl, $-(C_3-C_7)$cycloalkyl, $-(C_3-C_8)$cycloalkenyl, $-(C_1-C_6)$cyano alkyl, $-(C_1-C_6)$alkylene-hetero aryl, $-(C_1-C_6)$alkylene-aryl, aryl, heteroaryl, heterocycle, $-(C_0-C_6)$alkyl-$OR^{10}$, $-O-(C_2-C_6)$alkylene-$OR^{10}$, $-NR^{10}-(C_2-C_6)$alkylene-$OR^{10}$, $-(C_3-C_7)$cycloalkyl-$(C_1-C_6)$alkyl, $-O-(C_3-C_7)$cycloalkyl-$(C_1-C_6)$alkyl, $-NR^{10}-(C_3-C_7)$cycloalkyl-$(C_1-C_6)$alkyl, $-(C_1-C_6)$haloalkyl-$OR^{10}$, $-(C_1-C_6)$haloalkyl-$NR^{10}R^{11}$, $-(C_3-C_6)$alkynyl-$OR^{10}$, $-(C_3-C_6)$alkynyl-$NR^{10}R^{11}$, $-(C_3-C_6)$alkenyl-$OR^{10}$, $-(C_3-C_6)$alkenyl-$NR^{10}R^{11}$, $-(C_0-C_6)$alkyl-S-$R^{10}$, $-O-(C_2-C_6)$alkylene-S-$R^{10}$, $-NR^{10}-(C_2-C_6)$alkylene-S-$R^{11}$, $-(C_0-C_6)$alkyl-S(=O)-$R^{10}$, $-O-(C_1-C_6)$alkylene-S(=O)-$R^{10}$, $-NR^{10}-(C_1-C_6)$alkylene-S(=O)-$R^{11}$, $-(C_0-C_6)$alkyl-S(=O)$_2$-$R^{10}$, $-O-(C_1-C_6)$alkylene-S(=O)$_2$-$R^{10}$, $-NR^{10}-(C_1-C_6)$alkylene-S(=O)$_2$-$R^{11}$, $-(C_0-C_6)$alkyl-$NR^{10}R^{11}$, $-O-(C_2-C_6)$alkylene-$NR^{10}R^{11}$, $-NR^{10}-(C_2-C_6)$alkylene-$NR^{11}R^{12}$, $-(C_0-C_6)$alkyl-S(=O)$_2$$NR^{10}R^{11}$, $-O-(C_1-C_6)$alkylene-S(=O)$_2$$NR^{10}R^{11}$, $-NR^{10}-(C_1-C_6)$alkylene-S(=O)$_2$$NR^{11}R^{12}$, $-(C_0-C_6)$alkyl-$NR^{10}-S(=O)_2R^{11}$, $-O-(C_2-C_6)$alkylene-$NR^{10}-S(=O)_2R^{11}$, $-NR^{10}-(C_2-C_6)$alkylene-$NR^{11}-S(=O)_2R^{12}$, $-(C_0-C_6)$alkyl-C(=O)-$NR^{10}R^{11}$, $-O-(C_1-C_6)$alkylene-C(=O)-$NR^{10}R^{11}$, $-NR^{10}-(C_1-C_6)$alkylene-C(=O)-$NR^{11}R^{12}$, $-(C_0-C_6)$alkyl-$NR^{10}C(=O)-R^{11}$, $-O-(C_2-C_6)$alkylene-$NR^{10}C(=O)-R^{11}$, $-NR^{10}-(C_2-C_6)$alkylene-$NR^{11}C(=O)-R^{12}$, $-(C_0-C_6)$alkyl-OC(=O)-$R^{10}$, $-O-(C_2-C_6)$alkylene-OC(=O)-$R^{10}$, $-NR^{10}-(C_2-C_6)$alkylene-OC(=O)-$R^{11}$, $-(C_0-C_6)$alkyl-C(=O)-$OR^{10}$, $-O-(C_1-C_6)$alkylene-C(=O)-$OR^{10}$, $-NR^{10}-(C_1-C_6)$alkylene-C(=O)-$OR^{11}$, $-(C_0-C_6)$alkyl-C(=O)-$R^{10}$, $-O-(C_1-C_6)$alkylene-C(=O)-$R^{10}$, $-NR^{10}-(C_1-C_6)$alkylene-C(=O)-$R^{11}$, $-(C_0-C_6)$alkyl-$NR^{10}-C(=O)-OR^{11}$, $-(C_0-C_6)$alkyl-O-C(=O)-$NR^{10}R^{11}$, $-(C_0-C_6)$alkyl-$NR^{10}-C(=NR^{11})-NR^{12}R^{13}$, $-(C_0-C_6)$alkyl-$NR^{10}-C(=O)-NR^{11}R^{12}$, $-O-(C_2-C_6)$alkylene-$NR^{10}-C(=O)-NR^{11}R^{12}$, $-NR^{10}-(C_2-C_6)$alkylene-$NR^{11}-C(=O)-NR^{12}R^{13}$ and $-(C_0-C_6)$alkyl-$NR^{10}-C(=S)-NR^{11}R^{12}$;

$R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently selected from the group of hydrogen or an optionally substituted radical selected from the group of $-(C_1-C_6)$haloalkyl, $-(C_1-C_6)$alkyl, $-(C_1-C_6)$cyanoalkyl, $-(C_3-C_7)$cycloalkyl, $-(C_4-C_{10})$alkylene-cycloalkyl, heteroaryl, $-(C_1-C_6)$alkylene-heteroaryl, aryl, heterocycle and $-(C_1-C_6)$alkylene-aryl.

In a more preferred aspect of Formula (I), the invention provides a compound according to Formula (II):

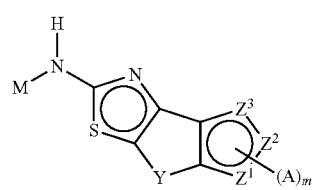

(II)

a pharmaceutically acceptable acid or base addition salt thereof, a stereochemically isomeric form thereof and an N-oxide form thereof.

In a more preferred aspect of Formula (I), the invention provides a compound according to Formula (III):

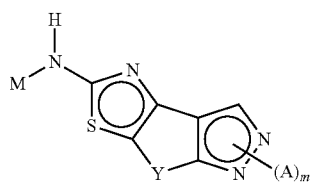
(III)

a pharmaceutically acceptable acid or base addition salt thereof, a stereochemically isomeric form thereof and an N-oxide form thereof.

In a preferred aspect, in any of Formulae (I), (II) and (III):
M is selected from an optionally substituted 3 to 10 membered ring selected from the group of aryl, heteroaryl and cycloalkyl;
Y is selected from the group of —$CR^4R^5$—$CR^6R^7$— and —$CR^4R^5$—$CR^6R^7$—$CR^8R^9$—;
m is 1;
$(A)_m$ radicals are each independently selected from the group of hydrogen and an optionally substituted radical selected from the group of —$(C_1$-$C_6)$alkyl and —$(C_0$-$C_6)$alkyl-C(=O)—$R^{10}$;
$R^1$, $R^2$, $R^3$, $R^4$, $R^5$, $R^6$, $R^7$, $R^8$, $R^9$ and $R^{10}$ are each independently selected from the group of hydrogen or an optionally substituted radical selected from the group of —$(C_1$-$C_6)$haloalkyl, —$(C_1$-$C_6)$alkyl, —$(C_1$-$C_6)$cyanoalkyl, —$(C_3$-$C_7)$cycloalkyl, —$(C_4$-$C_{10}$alkylene-cycloalkyl, heteroaryl, —$(C_1$-$C_6)$alkylene-heteroaryl, aryl, heterocycle and —$(C_1$-$C_6)$alkylene-aryl.

Particular preferred compounds of the invention are compounds as mentioned in the following list (List of Particular Preferred Compounds), as well as a pharmaceutically acceptable acid or base addition salt thereof, a stereochemically isomeric form thereof and an N-oxide form thereof:
N-(Pyridin-2-yl)-5,6-dihydro-4H-thiazolo[4,5-e]indazol-2-amine
2-Methyl-1-(2-(pyridin-2-ylamino)-4H-thiazolo[4,5-e]indazol-6(5H)-yl)propan-1-one
N-(6-Methylpyridin-2-yl)-5,6-dihydro-4H-thiazolo[4,5-e]indazol-2-amine
N-(6-Chloropyridin-2-yl)-5,6-dihydro-4H-thiazolo[4,5-e]indazol-2-amine
N-(2,5-Difluorophenyl)-5,6-dihydro-4H-thiazolo[4,5-e]indazol-2-amine
N-(6-Fluoropyridin-2-yl)-5,6-dihydro-4H-thiazolo[4,5-e]indazol-2-amine
4-Methyl-N-(pyridin-2-yl)-5,6-dihydro-4H-thiazolo[4,5-e]indazol-2-amine
Pyridin-2-yl-(4,5,6,7-tetrahydro-3-thia-1,7,8-triaza-cyclopenta[e]azulen-2-yl)-amine
4-Ethyl-N-(pyridin-2-yl)-5,6-dihydro-4H-thiazolo[4,5-e]indazol-2-amine
N-(3-Fluoropyridin-2-yl)-5,6-dihydro-4H-thiazolo[4,5-e]indazol-2-amine
(6-Methyl-pyridin-2-yl)-(4,5,6,7-tetrahydro-3-thia-1,7,8-triaza-cyclopenta[e]azulen-2-yl)-amine
(5-Fluoro-pyridin-2-yl)-(4,5,6,7-tetrahydro-3-thia-1,7,8-triaza-cyclopenta[e]azulen-2-yl)-amine
(3-Fluoro-pyridin-2-yl)-(4,5,6,7-tetrahydro-3-thia-1,7,8-triaza-cyclopenta[e]azulen-2-yl)-amine
(6-Methoxy-pyridin-2-yl)-(4,5,6,7-tetrahydro-3-thia-1,7,8-triaza-cyclopenta[e]azulen-2-yl)-amine
N-(5-Fluoropyridin-2-yl)-5,6-dihydro-4H-thiazolo[4,5-e]indazol-2-amine
(6-Chloro-pyridin-2-yl)-(4,5,6,7-tetrahydro-3-thia-1,7,8-triaza-cyclopenta[e]azulen-2-yl)-amine
N-(Pyrazin-2-yl)-5,6-dihydro-4H-thiazolo[4,5-e]indazol-2-amine
N-Cyclopentyl-5,6-dihydro-4H-thiazolo[4,5-e]indazol-2-amine
8-Methyl-N-(pyridin-2-yl)-5,6-dihydro-4H-thiazolo[4,5-e]indazol-2-amine
N-Cyclobutyl-5,6-dihydro-4H-thiazolo[4,5-e]indazol-2-amine
(6-Fluoro-pyridin-2-yl)-(4,5,6,7-tetrahydro-3-thia-1,7,8-triaza-cyclopenta[e]azulen-2-yl)-amine
Cyclopropyl-(4,5,6,7-tetrahydro-3-thia-1,7,8-triaza-cyclopenta[e]azulen-2-yl)-amine
Cyclobutyl-(4,5,6,7-tetrahydro-3-thia-1,7,8-triaza-cyclopenta[e]azulen-2-yl)-amine
Cyclopentyl-(4,5,6,7-tetrahydro-3-thia-1,7,8-triaza-cyclopenta[e]azulen-2-yl)-amine
Pyrimidin-2-yl-(4,5,6,7-tetrahydro-3-thia-1,7,8-triaza-cyclopenta[e]azulen-2-yl)-amine
N-(Pyrimidin-2-yl)-5,6-dihydro-4H-thiazolo[4,5-e]indazol-2-amine
(1-Methyl-1H-pyrazol-3-yl)-(4,5,6,7-tetrahydro-3-thia-1,7,8-triaza-cyclopenta[e]azulen-2-yl)-amine
N-(1-Methyl-1H-pyrazol-3-yl)-5,6-dihydro-4H-thiazolo[4,5-e]indazol-2-amine
N-(4-Methylpyrimidin-2-yl)-5,6-dihydro-4H-thiazolo[4,5-e]indazol-2-amine
(4-Methyl-pyrimidin-2-yl)-(4,5,6,7-tetrahydro-3-thia-1,7,8-triaza-cyclopenta[e]azulen-2-yl)-amine.
4,4-Dimethyl-N-(pyridin-2-yl)-5,6-dihydro-4H-thiazolo[4,5-e]indazol-2-amine
4,4-Dimethyl-N-(pyrimidin-2-yl)-5,6-dihydro-4H-thiazolo[4,5-e]indazol-2-amine
4-Methyl-N-(pyrimidin-2-yl)-5,6-dihydro-4H-thiazolo[4,5-e]indazol-2-amine and
5,5-Dimethyl-N-(pyrimidin-2-yl)-5,6-dihydro-4H-thiazolo[4,5-e]indazol-2-amine.

Definition of Terms

Listed below are definitions of various terms used in the specification and claims to describe the present invention.

For the avoidance of doubt it is to be understood that in this specification "$(C_1$-$C_6)$" means a carbon radical having 1, 2, 3, 4, 5 or 6 carbon atoms. "$(C_0$-$C_6)$" means a carbon radical having 0, 1, 2, 3, 4, 5 or 6 carbon atoms. In this specification "C" means a carbon atom, "N" means a nitrogen atom, "O" means an oxygen atom and "S" means a sulphur atom.

In the case where a subscript is the integer 0 (zero) the radical to which the subscript refers, indicates that the radical is absent, i.e. there is a direct bond between the radicals.

In this specification, unless stated otherwise, the term "bond" refers to a saturated covalent bond. When two or more bonds are adjacent to one another, they are assumed to be equal to one bond. For example, a radical -A-B—, wherein both A and B may be a bond, the radical is depicting a single bond.

In this specification, unless stated otherwise, the term "alkyl" includes both straight and branched chain alkyl radicals and may be methyl, ethyl, n-propyl, i-propyl, n-butyl, i-butyl, s-butyl, t-butyl, n-pentyl, i-pentyl, t-pentyl, neo-pentyl, n-hexyl, i-hexyl or t-hexyl. The term "$(C_0$-$C_3)$alkyl" refers to an alkyl radical having 0, 1, 2 or 3 carbon atoms and may be methyl, ethyl, n-propyl and i-propyl.

In this specification, unless stated otherwise, the term "alkylene" includes both straight and branched difunctional saturated hydrocarbon radicals and may be methylene, ethylene, n-propylene, i-propylene, n-butylene, i-butylene, s-butylene, t-butylene, n-pentylene, i-pentylene, t-pentylene, neopentylene, n-hexylene, i-hexylene or t-hexylene.

In this specification, unless stated otherwise, the term "cycloalkyl" refers to an optionally substituted carbocycle containing no heteroatoms, including mono-, bi-, and tricyclic saturated carbocycles, as well as fused ring systems. Such fused ring systems can include one ring that is partially or fully unsaturated such as a benzene ring to form fused ring systems such as benzo-fused carbocycles. Cycloalkyl includes such fused ring systems as spirofused ring systems. Examples of cycloalkyl include cyclopropyl, cyclobutyl, cyclopentyl, cyclohexyl, decahydronaphthalene, adamantane, indanyl, fluorenyl and 1,2,3,4-tetrahydronaphthalene and the like. The term "($C_3$-$C_7$)cycloalkyl" may be cyclopropyl, cyclobutyl, cyclopentyl, cyclohexyl, cycloheptyl and the like.

In this specification, unless stated otherwise, the term "alkenyl" includes both straight and branched chain alkenyl radicals. The term "($C_2$-$C_6$)alkenyl" refers to an alkenyl radical having 2 to 6 carbon atoms and one or two double bonds, and may be, but is not limited to vinyl, allyl, propenyl, i-propenyl, butenyl, i-butenyl, crotyl, pentenyl, i-pentenyl and hexenyl.

In this specification, unless stated otherwise, the term "alkynyl" includes both straight and branched chain alkynyl radicals. The term ($C_2$-$C_6$)alkynyl having 2 to 6 carbon atoms and one or two triple bonds, and may be, but is not limited to ethynyl, propargyl, butynyl, i-butynyl, pentynyl, i-pentynyl and hexynyl.

The term "aryl" refers to an optionally substituted monocyclic or bicyclic hydrocarbon ring system containing at least one unsaturated aromatic ring. Examples and suitable values of the term "aryl" are phenyl, naphthyl, 1,2,3,4-tetrahydronaphthyl, indyl, indenyl and the like.

In this specification, unless stated otherwise, the term "heteroaryl" refers to an optionally substituted monocyclic or bicyclic unsaturated, aromatic ring system containing at least one heteroatom selected independently from N, O or S. Examples of "heteroaryl" may be, but are not limited to thienyl, pyridyl, thiazolyl, isothiazolyl, furyl, pyrrolyl, triazolyl, imidazolyl, oxadiazolyl, oxazolyl, isoxazolyl, pyrazolyl, imidazolonyl, oxazolonyl, thiazolonyl, tetrazolyl, thiadiazolyl, benzoimidazolyl, benzooxazolyl, benzothiazolyl, tetrahydrotriazolopyridyl, tetrahydrotriazolopyrimidinyl, benzofuryl, benzothiophenyl, thionaphthyl, indolyl, isoindolyl, pyridonyl, pyridazinyl, pyrazinyl, pyrimidinyl, quinolyl, phtalazinyl, naphthyridinyl, quinoxalinyl, quinazolyl, imidazopyridyl, oxazo lopyridyl, thiazolopyridyl, imidazopyridazinyl, oxazolopyridazinyl, thiazolopyridazinyl, cynnolyl, pteridinyl, furazanyl, benzotriazolyl, pyrazolopyridinyl and purinyl.

In this specification, unless stated otherwise, the term "alkylene-aryl", "alkylene-heteroaryl" and "alkylene-cycloalkyl" refers respectively to a substituent that is attached via the alkyl radical to an aryl, heteroaryl or cycloalkyl radical, respectively. The term "($C_1$-$C_6$)alkylene-aryl" includes aryl-$C_1$-$C_6$-alkyl radicals such as benzyl, 1-phenylethyl, 2-phenylethyl, 1-phenylpropyl, 2-phenylpropyl, 3-phenylpropyl, 1-naphthylmethyl and 2-naphthylmethyl. The term "($C_1$-$C_6$)alkylene-heteroaryl" includes heteroaryl-$C_1$-$C_6$-alkyl radicals, wherein examples of heteroaryl are the same as those illustrated in the above definition, such as 2-furylmethyl, 3-furylmethyl, 2-thienylmethyl, 3-thienylmethyl, 1-imidazolylmethyl, 2-imidazolylmethyl, 3-imidazolylmethyl, 2-oxazolylmethyl, 3-oxazolylmethyl, 2-thiazolylmethyl, 3-thiazolylmethyl, 2-pyridylmethyl, 3-pyridylmethyl, 4-pyridylmethyl, 1-quinolylmethyl or the like.

In this specification, unless stated otherwise, the term "heterocycle" refers to an optionally substituted, monocyclic or bicyclic saturated, partially saturated or unsaturated ring system containing at least one heteroatom selected independently from N, O and S.

In this specification, unless stated otherwise, a 5- or 6-membered ring containing one or more atoms independently selected from C, N, O and S, includes aromatic and heteroaromatic rings as well as carbocyclic and heterocyclic rings which may be saturated or unsaturated. Examples of such rings may be, but are not limited to, furyl, isoxazolyl, isothiazolyl, oxazolyl, pyrazinyl, pyrazolyl, pyridazinyl, pyridyl, pyrimidyl, pyrrolyl, thiazolyl, thienyl, imidazolyl, imidazolidinyl, imidazolinyl, triazolyl, morpholinyl, piperazinyl, piperidyl, piperidonyl, pyrazolidinyl, pyrazolinyl, pyrrolidinyl, pyrrolinyl, tetrahydropyranyl, tetrahydrothiopyranyl, oxazolidinonyl, thiomorpholinyl, oxadiazolyl, thiadiazolyl, tetrazolyl, phenyl, cyclohexyl, cyclopentyl, cyclohexenyl and cyclopentenyl.

In this specification, unless stated otherwise, a 3- to 10-membered ring containing one or more atoms independently selected from C, N, O and S, includes aromatic and heteroaromatic rings as well as carbocyclic and heterocyclic rings which may be saturated or unsaturated. Examples of such rings may be, but are not limited to imidazolidinyl, imidazolinyl, morpholinyl, piperazinyl, piperidyl, piperidonyl, pyrazolidinyl, pyrazolinyl, pyrrolidinyl, pyrrolinyl, tetrahydropyranyl, thiomorpholinyl, tetrahydrothiopyranyl, furyl, pyrrolyl, isoxazolyl, isothiazolyl, oxazolyl, oxazolidinonyl, pyrazinyl, pyrazolyl, pyridazinyl, pyridyl, pyrimidyl, pyrrolyl, thiazolyl, thienyl, imidazolyl, triazolyl, phenyl, cyclopropyl, aziridinyl, cyclobutyl, azetidinyl, oxadiazolyl, thiadiazolyl, tetrazolyl, cyclopentyl, cyclopentenyl, cyclohexyl, cyclohexenyl, cycloheptyl, cycloheptenyl, cyclooctyl and cyclooctenyl.

In this specification, unless stated otherwise, the term "halo" or "halogen" may be fluoro, chloro, bromo or iodo.

In this specification, unless stated otherwise, the term "haloalkyl" means an alkyl radical as defined above, substituted with one or more halo radicals. The term "($C_1$-$C_6$) haloalkyl" may include, but is not limited to, fluoromethyl, difluoromethyl, trifluoromethyl, fluoroethyl and difluoroethyl. The term "O—$C_1$-$C_6$-haloalkyl" may include, but is not limited to, fluoromethoxy, difluoromethoxy, trifluoromethoxy and fluoroethoxy.

In this specification, unless stated otherwise, the term "haloalkylene" means an alkylene radical as defined above, substituted with one or more halo radicals. The term "($C_1$-$C_6$)haloalkylene" may include, but is not limited to, fluoromethylene, difluoromethylene, fluoroethylene and difluoroethylene. The term "O—$C_1$-$C_6$-haloalkylene" may include, but is not limited to, fluoromethylenoxy, difluoromethylenoxy and fluoroethylenoxy.

In this specification, unless stated otherwise, the term "cyanoalkyl" means an alkyl radical as defined above, substituted with one or more cyano.

In this specification, unless stated otherwise, the term "cyanoalkylene" means an alkylene radical as defined above, substituted with one or more cyano.

In this specification, unless stated otherwise, the term "optionally substituted" refers to radicals further bearing one or more substituents which may be, ($C_1$-$C_6$)alkyl, hydroxy, ($C_1$-$C_6$)alkylene-oxy, mercapto, aryl, heterocycle, halogen, trifluoromethyl, pentafluoroethyl, cyano, cyanomethyl, nitro, amino, amido, amidinyl, carboxyl, carboxamide, ($C_1$-$C_6$) alkylene-oxycarbonyl, carbamate, sulfonamide, ester and sulfonyl.

In this specification, unless stated otherwise, the term "solvate" refers to a complex of variable stoichiometry formed by a solute (e.g. a compound of Formula (I)) and a solvent. The solvent is a pharmaceutically acceptable solvent as preferably water; such solvent may not interfere with the biological activity of the solute.

In this specification, unless stated otherwise, the term "positive allosteric modulator of mGluR4" or "allosteric modulator of mGluR4" refers also to a pharmaceutically acceptable acid or base addition salt thereof, a stereochemically isomeric form thereof and an N-oxide form thereof.

In one embodiment, the term "compound" also embraces or includes pharmaceutically acceptable acid or base addition salts thereof, and/or stereochemically isomeric forms thereof and/or N-oxide forms thereof.

Pharmaceutical Compositions

Allosteric modulators of mGluR4 described herein, and the pharmaceutically acceptable salts, solvates and hydrates thereof can be used in pharmaceutical preparations in combination with a pharmaceutically acceptable carrier or diluent. Suitable pharmaceutically acceptable carriers include inert solid fillers or diluents and sterile aqueous or organic solutions. The allosteric modulators of mGluR4 will be present in such pharmaceutical compositions in amounts sufficient to provide the desired dosage amount in the range described herein. Techniques for formulation and administration of the compounds of the instant invention can be found in *Remington: the Science and Practice of Pharmacy*, 19$^{th}$ edition, Mack Publishing Co., Easton, Pa. (1995).

The amount of allosteric modulators of mGluR4, administered to the subject will depend on the type and severity of the disease or condition and on the characteristics of the subject, such as general health, age, sex, body weight and tolerance to drugs. The skilled artisan will be able to determine appropriate dosages depending on these and other factors. Effective dosages for commonly used CNS drugs are well known to the skilled person. The total daily dose usually ranges from about 0.05-2000 mg.

The present invention relates to pharmaceutical compositions which provide from about 0.01 to 1000 mg of the active ingredient per unit dose. The compositions may be administered by any suitable route. For example orally in the form of capsules and the like, parenterally in the form of solutions for injection, topically in the form of onguents or lotions, ocularly in the form of eye-drops, rectally in the form of suppositories, intranasally or transcutaneously in the form of delivery system like patches.

For oral administration, the allosteric modulators of mGluR4 thereof can be combined with a suitable solid or liquid carrier or diluent to form capsules, tablets, pills, powders, syrups, solutions, suspensions and the like.

The tablets, pills, capsules, and the like contain from about 0.01 to about 99 weight percent of the active ingredient and a binder such as gum tragacanth, acacias, corn starch or gelatin; excipients such as dicalcium phosphate; a disintegrating agent such as corn starch, potato starch, alginic acid, a lubricant such as magnesium stearate; and a sweetening agent such as sucrose, lactose or saccharin. When a dosage unit form is a capsule, it may contain, in addition to materials of the above type, a liquid carrier such as a fatty oil.

Various other materials may be present as coatings or to modify the physical form of the dosage unit. For instance, tablets may be coated with shellac, sugar or both. A syrup or elixir may contain, in addition to the active ingredient, sucrose as a sweetening agent, methyl and propylparabens as preservatives, a dye and a flavoring such as cherry or orange flavor.

For parenteral administration the disclosed allosteric modulators of mGluR4 can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable salts of the compounds. Dispersions can also be prepared in glycerol, liquid polyethylene glycols and mixtures thereof in oils. Under ordinary conditions of storage and use, these preparations contain a preservative to prevent the growth of microorganisms.

In addition, to the formulations described previously, the compounds may also be formulated as a depot preparation. Such long acting formulations may be administered by implantation, for example, subcutaneously or intramuscularly or by intramuscular injection. Thus, for example, as an emulsion in an acceptable oil, or ion exchange resins, or as sparingly soluble derivatives, for example, as sparingly soluble salts.

Preferably disclosed allosteric modulators of mGluR4 or pharmaceutical formulations containing these compounds are in unit dosage form for administration to a mammal. The unit dosage form can be any unit dosage form known in the art including, for example, a capsule, an IV bag, a tablet, or a vial. The quantity of active ingredient in a unit dose of composition is an effective amount and may be varied according to the particular treatment involved. It may be appreciated that it may be necessary to make routine variations to the dosage depending on the age and condition of the patient. The dosage will also depend on the route of administration which may be by a variety of routes including oral, aerosol, rectal, transdermal, subcutaneous, intravenous, intramuscular, intraperitoneal and intranasal.

Classical treatment of Parkinsonism typically involves the use of levodopa combined with carbidopa (SINEMET™) or benserazide (MADOPAR™). Dopamine agonists such as bromocriptine (PARLODEL™), lisuride and pergolide (CELANCE™) act directly on dopamine receptors and are also used for the treatment of Parkinsonism.

Methods of Synthesis

The compounds according to the invention, in particular the compounds according to the Formula (I) to (III), may be prepared by methods known in the art of organic synthesis as set forth in part by the following synthesis schemes. In all of the schemes described below, it is well understood that protecting groups for sensitive or reactive groups are employed where necessary in accordance with general principles of chemistry. Protecting groups are manipulated according to standard methods of organic synthesis (Green T. W. and Wuts P. G. M., (1991) *Protecting Groups in Organic Synthesis*, John Wiley & Sons). These groups are removed at a convenient stage of the compound synthesis using methods that are readily apparent to those skilled in the art. The selection of process as well as the reaction conditions and order of their execution shall be consistent with the preparation of compounds of Formula (I) to (III).

The compounds according to the invention may be represented as a mixture of enantiomers, which may be resolved into the individual pure R- or S-enantiomers. If for instance, a particular enantiomer is required, it may be prepared by asymmetric synthesis or by derivation with a chiral auxiliary, where the resulting diastereomeric mixture is separated and the auxiliary group cleaved to provide the pure desired enantiomers. Alternatively, where the molecule contains a basic functional group such as an amino or an acidic functional group such as carboxyl, this resolution may be conveniently performed by fractional crystallization from various solvents as the salts of an optical active acid or by other methods known in the literature (e.g. chiral column chromatography).

Resolution of the final product, an intermediate or a starting material may be performed by any suitable method known in the art (Eliel E. L., Wilen S. H. and Mander L. N., (1984) *Stereochemistry of Organic Compounds*, Wiley-Interscience).

Many of the heterocyclic compounds of the invention can be prepared using synthetic routes well known in the art (Katrizky A. R. and. Rees C. W., (1984) *Comprehensive Heterocyclic Chemistry*, Pergamon Press).

The product from the reaction can be isolated and purified employing standard techniques, such as extraction, chromatography, crystallization and distillation.

The compounds of the invention may be prepared by general route of synthesis as disclosed in the following methods.

In one embodiment of the present invention compounds of Formula (III) may be prepared according to the synthetic sequences illustrated in Scheme 1. Pyrazole g3 can be synthesized from cyclohexane-1,3-dione g1 which is condensed with 1,1-dimethoxy-N,N-dimethylmethanamine followed by cyclization in the presence of hydrazine. Then compound g3, in the presence of pyridinium tribromide, can be transformed into bromoketone g4 which undergoes cyclization with thiourea g5 to yield aminothiazole g6.

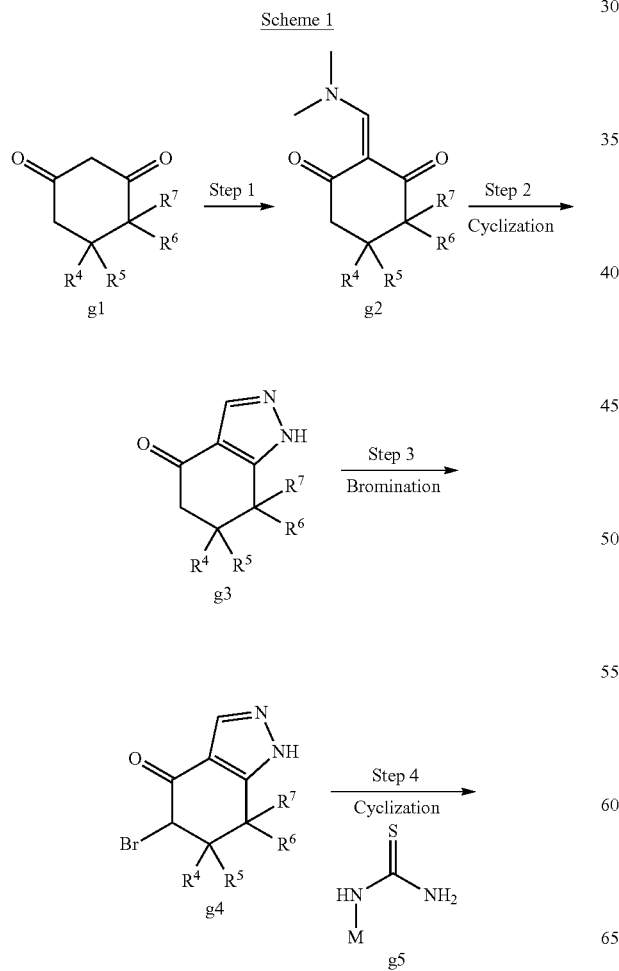

In one embodiment of the present invention compounds of Formula (III) may be prepared according to the synthetic sequences illustrated in Scheme 2. Pyrazole g3 can be prepared from cyclohexane-1,3-dione g1 which is condensed with 1,1-dimethoxy-N,N-dimethylmethanamine followed by cyclization, under acidic conditions, in the presence of hydrazine. Then compound g3, in the presence of pyridinium tribromide, can be transformed into dibromoketone g7 which undergoes cyclization with thiourea g5 to yield aminothiazole g6.

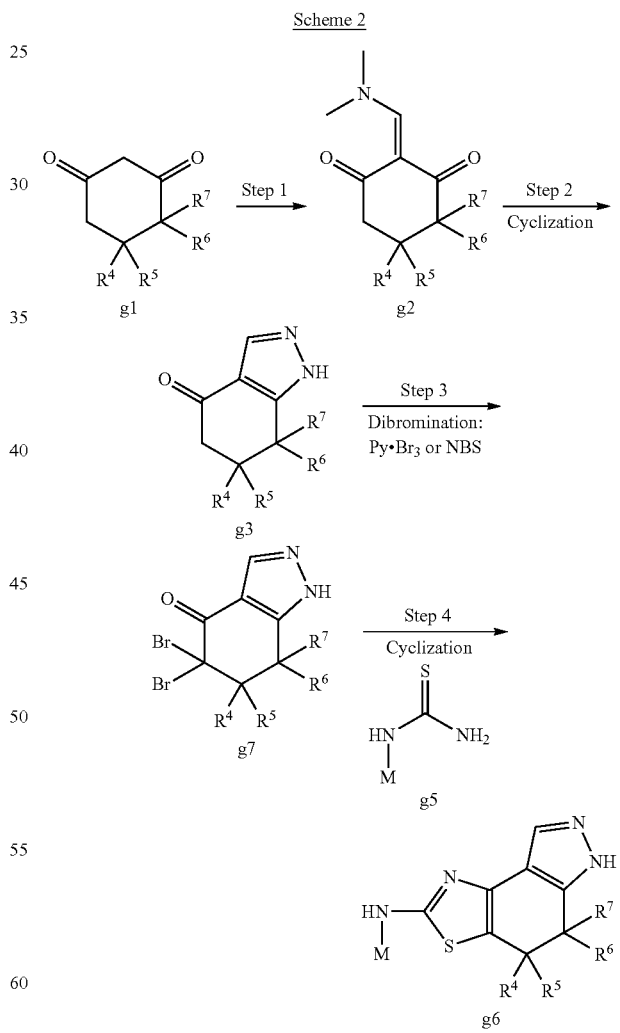

In one embodiment of the present invention compounds of Formula (III) may be prepared according to the synthetic sequences illustrated in Scheme 3. Pyrazole g9 can be synthesized from enamine g2 which is transformed into tosylhydrazide and cyclized. Then compound g9, in the presence of N-bromosuccinimide, can be transformed into bromoketone g10 which undergoes at the same time cyclization with thiourea g5 and deprotection to yield aminothiazole g6.

g11 is monoacylated under classical conditions and is rearranged into ketone g13. Then, in the presence of hydrazine, compound g13 can be cyclized into pyrazole g14. Double bromination of ketone g14, in the presence of bromine, allows cyclization with thiourea g5 into aminothiazole g16.

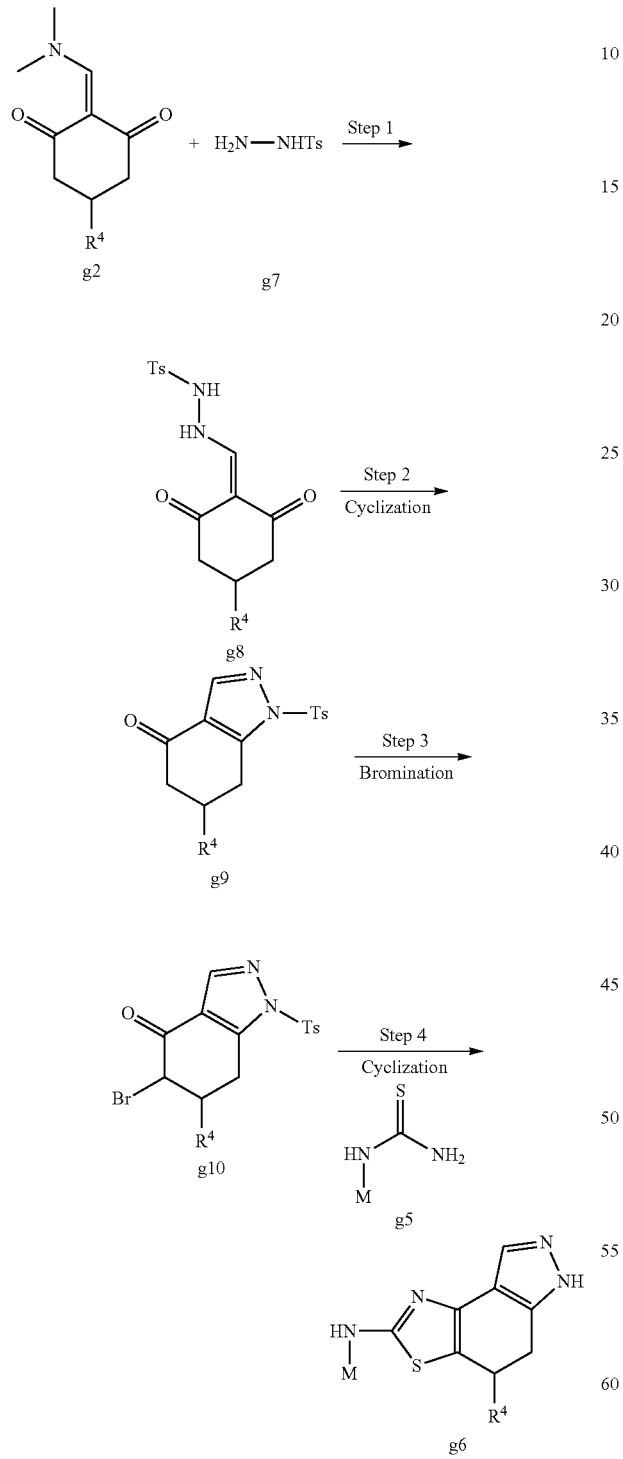

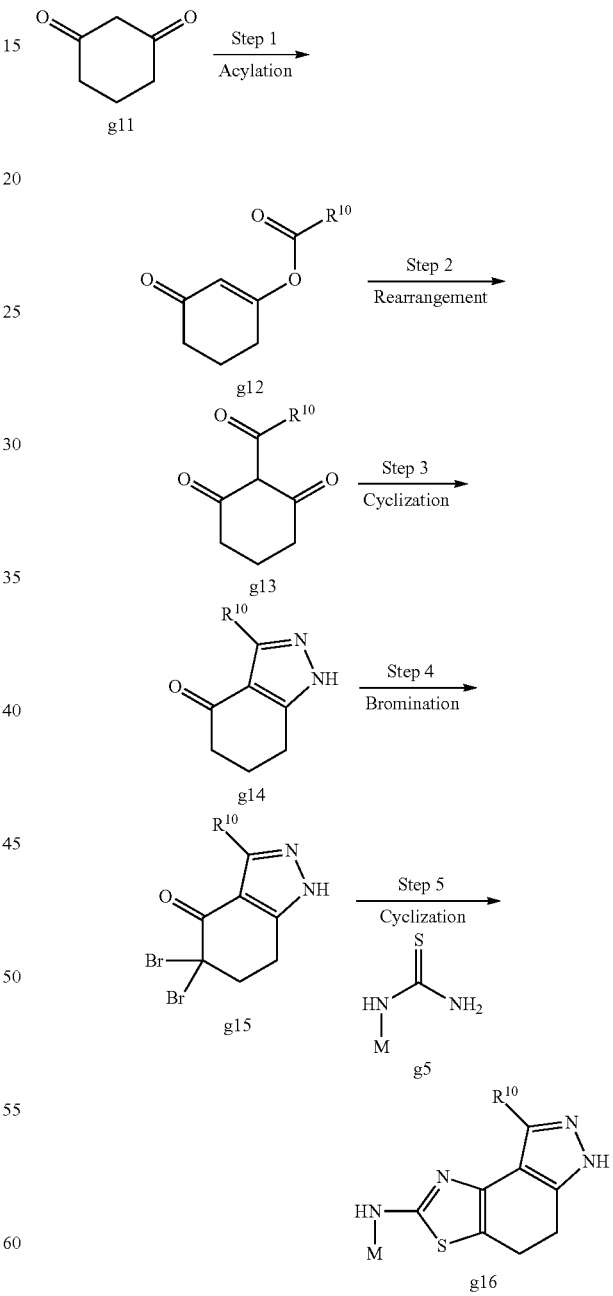

In one embodiment of the present invention compounds of Formula (III) may be prepared according to the synthetic sequences illustrated in Scheme 4. Cyclohexane-1,3-dione In one embodiment of the present invention compounds of Formula (III) may be prepared according to Scheme 5. g6 as described above, may be acylated by acetyl chloride to yield pyrazole g17.

Scheme 5 g6

Acylation → g17

Experimental

Unless otherwise noted, all starting materials were obtained from commercial suppliers and used without further purification.

Specifically, the following abbreviations may be used in the examples and throughout the specification.

| | |
|---|---|
| $AlCl_3$ (Aluminum trichloride) | mmol (Millimoles) |
| AcOEt (Ethyl acetate) | M.p. (Melting point) |
| $CHCl_3$ (Chloroform) | NBS (N-Bromosuccinimide) |
| DCM (Dichloromethane) | NaCl (Sodium chloride) |
| EtOH (Ethanol) | $NaHCO_3$ (Sodium hydrogenocarbonate) |
| $Et_2O$ (Diethyl ether) | NaOH (Sodium hydroxide) |
| HCl (Hydrochloric acid) | $Na_2CO_3$ (Sodium carbonate) |
| $H_2SO_4$ (Sulfuric acid) | $Na_2SO_4$ (Sodium sulphate) |
| LC-MS (Liquid Chromatography Mass Spectrum) | $Na_2S_2O_3$ (Sodium sulfite) |
| M (Molar) | RT (Retention Time) |
| MeOH (Methanol) | TLC (Thin layer chromatography) |
| mg (Milligrams) | THF (Tetrahydrofuran) |
| $MgSO_4$ (Magnesium sulphate) | UPLC-MS (Ultra Performance Liquid Chromatography Mass Spectrum) |
| mL (Milliliters) | |

All references to brine refer to a saturated aqueous solution of NaCl. Unless otherwise indicated, all temperatures are expressed in ° C. (degrees Centigrade). All reactions are conducted not under an inert atmosphere at room temperature unless otherwise noted.

Most of the reaction were monitored by thin-layer chromatography on 0.25 mm Merck silica gel plates (60F-254), visualized with UV light. Flash column chromatography was performed on prepacked silica gel cartridges (15-40 μM, Merck).

Melting point determination was performed on a Buchi B-540 apparatus.

EXAMPLES

Example 1

N-(Pyridin-2-yl)-5,6-dihydro-4H-thiazolo[4,5-e]indazol-2-amine (Final Compound 1-1)

2-((Dimethylamino)methylene)cyclohexane-1,3-dione

According to Scheme 1 Step 1: A solution of cyclohexane-1,3-dione (89 mmol, 10 g) and of 1,1-dimethoxy-N,N-dimethylmethanamine (263 mmol, 35.0 mL) was stirred under reflux for 2 hours. After evaporation, 14.8 g (88.5 mmol, 99%) of 2-((dimethylamino)methylene)cyclohexane-1,3-dione were obtained as a yellow solid.

UPLC-MS: RT=0.31 min; MS m/z $ES^+$=168.

6,7-Dihydro-1H-indazol-4(5H)-one

According to Scheme 1 Step 2: A solution of hydrazine hydrochloride (41.9 mmol, 2.87 g), NaOH (6 M, 42 mmol, 7.0 mL) in MeOH (100 mL) was added, at 0° C., to a solution of 2-((dimethylamino)methylene)cyclohexane-1,3-dione (41.9 mmol, 7.00 g) and the reaction mixture was stirred under reflux for 3 hours. After evaporation, water was added and the aqueous phase was extracted with AcOEt at 50° C. The organic phase was dried over $Na_2SO_4$, was filtered and was concentrated under reduced pressure to yield 6,7-dihydro-1H-indazol-4(5H)-one (36.7 mmol, 5.00 g, 88%) as a yellow powder.

LC-MS: RT=1.37 min; MS m/z $ES^+$=137.

5-Bromo-6,7-dihydro-1H-indazol-4(5H)-one

According to Scheme 1 Step 3: Pyridinium tribromide (25.7 mmol, 8.22 g) was added to a solution of 6,7-dihydro-1H-indazol-4(5H)-one (25.7 mmol, 3.50 g) in acetic acid (60 mL) and the reaction mixture was stirred under reflux for 2 hours. After evaporation of the solvent, the crude residue was partitioned between DCM and a saturated solution of $Na_2S_2O_3$. The organic phase was washed with a saturated solution of $Na_2CO_3$ and with water, was dried over $Na_2SO_4$ and concentrated to yield 5-bromo-6,7-dihydro-1H-indazol-4(5H)-one (23.3 mmol, 5.00 g, 90%).

UPLC-MS: RT=0.48 min; MS m/z $ES^+$=216.

N-(Pyridin-2-yl)-5,6-dihydro-4H-thiazolo[4,5-e]indazol-2-amine

According to Scheme 1 Step 4: A solution of 5-bromo-6,7-dihydro-1H-indazol-4(5H)-one (23.3 mmol, 5.00 g) and of 1-(pyridin-2-yl)thiourea (20.9 mmol, 3.21 g) in acetone (60 mL) was stirred at 60° C. for 5 hours. The precipitate formed was filtered and partitioned between AcOEt and a saturated solution of $NaHCO_3$. The aqueous phase was extracted with AcOEt. The organic phase was dried over $Na_2SO_4$ and concentrated to yield a grey solid. The crude residue was purified by flash chromatography over silica gel using DCM/MeOH (95:5) as eluent and by two recristallizations with AcOEt/MeOH (50:50) to yield N-(pyridin-2-yl)-5,6-dihydro-4H-thiazolo[4,5-e]indazol-2-amine (11.9 mmol, 3.20 g, 51%) as a white solid.

M.p.: 297-299° C.;
UPLC-MS: RT=0.60 min; MS m/z $ES^+$=270.

Example 2

4,4-Dimethyl-N-(pyrimidin-2-yl)-5,6-dihydro-4H-thiazolo[4,5-e]indazol-2-amine (Final Compound 1-32)

2-((Dimethylamino)methylene)-5,5-dimethylcyclohexane-1,3-dione

According to Scheme 2 Step 1: A solution of 5,5-dimethylcyclohexane-1,3-dione (428 mmol, 60 g) and of 1,1-dimethoxy-N,N-dimethylmethanamine (514 mmol, 68.2 mL) was stirred at room temperature for 1 hour. After evaporation and trituration in cyclohexane, 38.5 g (197 mmol, 46%) of 2-((dimethylamino)methylene)-5,5-dimethylcyclohexane-1,3-dione were obtained as a pale yellow solid.

UPLC-MS: RT=0.47 min; MS m/z ES$^+$=196.

6,6-Dimethyl-6,7-dihydro-1H-indazol-4(5H)-one

According to Scheme 2 Step 2: At 0° C., acetic acid (8.55 mL) followed by hydrazine monohydrate (197 mmol, 11.3 mL), were added slowly to a solution of 2-((dimethylamino)methylene)-5,5-dimethylcyclohexane-1,3-dione (197 mmol, 38.5 g) in butanol (400 mL). The reaction mixture was stirred under reflux for 16 hours. After evaporation of the filtrate, the crude residue was purified by flash chromatography over silica gel cyclohexane/AcOEt (100:0 to 50:50) and then over $C_{18}$ gel using water/MeOH (100:0 to 50:50) as eluent to yield 6,6-dimethyl-6,7-dihydro-1H-indazol-4(5H)-one (76.7 mmol, 12.6 g, 39%) as a pale yellow solid.

LC-MS: RT=0.53 min; MS m/z ES$^+$=165.

5,5-Dibromo-6,6-dimethyl-6,7-dihydro-1,1-indazol-4(5H)-one

According to Scheme 2 Step 3: Pyridinium tribromide (15.2 mmol, 4.87 g) was added to a solution of 6,6-dimethyl-6,7-dihydro-1H-indazol-4(5H)-one (6.09 mmol, 1.00 g) in acetic acid (9 mL) and the reaction mixture was heated under reflux for 3 hours. After evaporation of the solvent, the crude residue was partitioned between DCM and a saturated solution of $Na_2CO_3$. The organic phase was washed with water, was dried over $Na_2SO_4$ and concentrated to yield 5,5-dibromo-6,6-dimethyl-6,7-dihydro-1H-indazol-4(5H)-one (6.09 mmol, 1.96 g, 100%).

UPLC-MS: RT=0.81 min; MS m/z ES$^+$=323.

4,4-Dimethyl-N-(pyrimidin-2-yl)-5,6-dihydro-4H-thiazolo[4,5-e]indazol-2-amine

According to Scheme 2 Step 4: A solution of 5,5-dibromo-6,6-dimethyl-6,7-dihydro-1H-indazol-4(5H)-one (6.09 mmol, 1.96 g) and of 1-(pyrimidin-2-yl)thiourea (7.31 mmol, 1.13 g) in ethanol (15 mL) was microwaved at 150° C. for 90 minutes and then at 140° C. for 40 minutes. After filtration, the reaction mixture was concentrated to dryness. The crude residue was partitioned between DCM and a saturated solution of $Na_2CO_3$. The aqueous phase was extracted with DCM. The organic phase was dried over $Na_2SO_4$ and concentrated. The crude residue was purified by flash chromatography over silica gel using DCM/MeOH (98:2 to 90:10) as eluent to yield 4,4-dimethyl-N-(pyrimidin-2-yl)-5,6-dihydro-4H-thiazolo[4,5-e]indazol-2-amine (0.10 mmol, 31 mg) as a brown solid.

UPLC-MS: RT=0.74 min; MS m/z ES$^+$=299.

Example 3

5,5-Dimethyl-N-(pyrimidin-2-yl)-5,6-dihydro-4H-thiazolo[4,5-e]indazol-2-amine (Final Compound 1-34)

2-((Dimethylamino)methylene)-4,4-dimethylcyclohexane-1,3-dione

According to Scheme 2 Step 1: A solution of 4,4-dimethylcyclohexane-1,3-dione (157 mmol, 22 g) and of 1,1-dimethoxy-N,N-dimethylmethanamine (235 mmol, 31.3 mL) was stirred at room temperature for 1 hour. After evaporation and trituration in petroleum ether, 29.2 g (150 mmol, 95%) of 2-((dimethylamino)methylene)-4,4-dimethylcyclohexane-1,3-dione were obtained as a pale orange solid.

UPLC-MS: RT=0.50 min; MS m/z ES$^+$=196.

7,7-Dimethyl-6,7-dihydro-1H-indazol-4(5H)-one

According to Scheme 2 Step 2: At 0° C., acetic acid (8.55 mL) followed by hydrazine monohydrate (150 mmol, 7.25 mL), were added slowly to a solution of 2-((dimethylamino)methylene)-4,4-dimethylcyclohexane-1,3-dione (150 mmol, 29.2 g) in butanol (400 mL). The reaction mixture was stirred under reflux for 16 hours. After evaporation of the filtrate, the crude residue was purified by flash chromatography over silica gel cyclohexane/AcOEt (100:0 to 50:50) and then over $C_{18}$ gel using water/MeOH (100:0 to 50:50) as eluent to yield 7,7-dimethyl-6,7-dihydro-1H-indazol-4(5H)-one (76.7 mmol, 12.6 g, 51%) as a pale yellow solid.

LC-MS: RT=0.53 min; MS m/z ES$^+$=165.

5,5-Dibromo-7,7-dimethyl-6,7-dihydro-1H-indazol-4(5H)-one

According to Scheme 2 Step 3: NBS (3.65 mmol, 650 mg) was added to a solution of 7,7-dimethyl-6,7-dihydro-1H-indazol-4(5H)-one (1.83 mmol, 300 mg) in chloroform (4 mL). The reaction mixture was stirred at 70° C. for 3 hours. As there was still some starting material, some NBS (3.65 mmol, 650 mg) was added and the reaction mixture was stirred for 12 hours. To complete the conversion of the monobrominated compound into the dibrominated one, some NBS (1.85 mmol, 330 mg) was added and the reaction mixture was stirred for 4 hours under reflux. After cooling to room temperature, the reaction mixture was diluted with DCM and a saturated solution of $Na_2CO_3$ was added. The organic phase was washed with water, was dried over $Na_2SO_4$ and concentrated to yield 5,5-dibromo-7,7-dimethyl-6,7-dihydro-1H-indazol-4(5H) one and 5-bromo-7,7-dimethyl-6,7-dihydro-1H-indazol-4(5H)one (727 mg).

UPLC-MS: RT=0.80 min; MS m/z ES$^+$=323.

5,5-Dimethyl-N-(pyrimidin-2-yl)-5,6-dihydro-4H-thiazolo[4,5-e]indazol-2-amine

According to Scheme 2 Step 4: A solution of 5,5-dibromo-7,7-dimethyl-6,7-dihydro-1H-indazol-4(5H)-one (6.09 mmol, 1.96 g) and of 1-(pyrimidin-2-yl)thiourea (6.09 mmol, 939 mg) in ethanol (18 mL) was microwaved at 150° C. for 90 minutes and then at 140° C. for 40 minutes. After filtration, the reaction mixture was concentrated to dryness. The crude residue was partitioned between DCM and a saturated solution of $Na_2CO_3$. The aqueous phase was extracted with DCM. The organic phase was dried over $Na_2SO_4$ and concentrated. The crude residue was purified by flash chromatography over silica gel using DCM/MeOH (98:2 to 90:10) as eluent to yield 5,5-dimethyl-N-(pyrimidin-2-yl)-5,6-dihydro-4H-thiazolo [4,5-e]indazol-2-amine (90 mol, 27 mg) as a brown solid.

UPLC-MS: RT=0.76 min; MS m/z ES$^+$=299.

Example 4

N-(6-Methylpyridin-2-yl)-5,6-dihydro-4H-thiazolo[4,5-e]indazol-2-amine (Final Compound 1-3)

N'-((2,6-Dioxocyclohexylidene)methyl)-4-methylbenzenesulfonohydrazide

According to Scheme 3 Step 1: 4-Methylbenzenesulfonohydrazide (44.6 mmol, 8.31 g) was added to a solution of 2-((dimethylamino)methylene)cyclohexane-1,3-dione (44.6 mmol, 7.46 g) in EtOH (50 mL) and the reaction mixture was stirred at room temperature for 5 minutes. After evaporation, 13.8 g (44.6 mmol, 100%) of N'-((2,6-dioxocyclohexylidene)methyl)-4-methylbenzenesulfonohydrazide were obtained as an orange oil.

LC-MS: RT=2.16 min; MS m/z ES$^+$=309.

1-Tosyl-6,7-dihydro-1H-indazol-4(5H)-one

According to Scheme 3 Step 2: A solution of N4(2,6-dioxocyclohexylidene)methyl)-4-methylbenzenesulfonohydrazide (32.4 mmol, 10.0 g) in EtOH (10 mL) was stirred at 80° C. for 15 hours. After evaporation, water was added and the aqueous phase was extracted with DCM. The organic phase was dried over Na$_2$SO$_4$, was filtered and was concentrated. The crude residue was purified by flash chromatography over silica gel using DCM as eluent to yield 1-tosyl-6,7-dihydro-1H-indazol-4(5H)-one (6.89 mmol, 2.00 g, 21%) as an orange solid.

LC-MS: RT=2.19 min; MS m/z ES$^+$=291.

5-Bromo-1-tosyl-6,7-dihydro-1H-indazol-4(5H)-one

According to Scheme 3 Step 3: N-Bromosuccinimide (3.44 mmol, 613 mg) was added to a solution of 1-tosyl-6,7-dihydro-1H-indazol-4(5H)-one (3.44 mmol, 1.00 g) in DCM (10 mL) and the reaction mixture was stirred at room temperature for 12 hours. A solution of NaHCO$_3$ was added to the reaction mixture and the aqueous phase was extracted with DCM. The organic phase was dried over Na$_2$SO$_4$ and concentrated to yield 5-bromo-1-tosyl-6,7-dihydro-1H-indazol-4(5H)-one (2.44 mmol, 900 mg, 42%) as an orange oil.

LC-MS: RT=2.60 min; MS m/z ES$^+$=371.

N-(6-Methylpyridin-2-yl)-5,6-dihydro-4H-thiazolo[4,5-e]indazol-2-amine

According to Scheme 3 Step 4: A solution of 5-bromo-1-tosyl-6,7-dihydro-1H-indazol-4(5H)-one (0.90 mmol, 331 mg) and of 1-(6-methylpyridin-2-yl)thiourea (0.90 mmol, 150 mg) in EtOH (10 mL) and HCl (35%, 1 mL) was stirred at 80° C. for 5 hours. The reaction was quenched with the addition of a saturated solution of NaHCO$_3$ at room temperature until pH=8. The aqueous phase was extracted with DCM. The organic phase was dried over Na$_2$SO$_4$ and concentrated. The crude residue was washed with Et$_2$O and dried to yield N-(6-methylpyridin-2-yl)-5,6-dihydro-4H-thiazolo[4,5-e]indazol-2-amine (0.78 mmol, 220 mg, 87%) as a white solid.

M.p.: 280° C.;
LC-MS: RT=1.71 min; MS m/z ES$^+$=284.

Example 5

8-Methyl-N-(pyridin-2-yl)-5,6-dihydro-4H-thiazolo[4,5-e]indazol-2-amine (Final Compound 1-19)

3-Oxocyclohex-1-enyl acetate

According to Scheme 4 Step 1: Acetyl chloride (19.6 mmol, 1.39 mL) was added to a solution of cyclohexane-1,3-dione (17.8 mmol, 2.00 g) and pyridine (17.8 mmol, 1.28 mL) in CHCl$_3$ (60 mL) and the reaction mixture was stirred at room temperature for 2 hours. The reaction was quenched with the addition of water and the organic phase was washed with a solution of HCl (0.1 M, 30 mL), a saturated solution of NaHCO$_3$ (30 mL) and water (30 mL). The organic phase was dried over Na$_2$SO$_4$ and concentrated to yield 3-oxocyclohex-1-enyl acetate (13.2 mmol, 2.04 g, 74%) as a yellow oil.

UPLC-MS: RT=0.60 min; MS m/z ES$^+$=155.

2-Acetylcyclohexane-1,3-dione

According to Scheme 4 Step 2: AlCl$_3$ (26.5 mmol, 3.53 g) was added to a solution of 3-oxocyclohex-1-enyl acetate (13.2 mmol, 2.04 g) in dichloroethane (10 mL) and the reaction mixture was stirred at room temperature for 2 hours. The reaction mixture was poured onto a solution of H$_2$SO$_4$ in ice. The aqueous phase was extracted with CHCl$_3$ (50 mL). The organic phase was washed with water, dried over Na$_2$SO$_4$, was filtered and was concentrated to yield 2-acetylcyclohexane-1,3-dione (7.78 mmol, 1.20 g, 59%) as a yellow oil.

UPLC-MS: RT=0.69 min; MS m/z ES$^+$=155.

3-Methyl-6,7-dihydro-1H-indazol-4(5H)-one

According to Scheme 4 Step 3: Hydrazine monohydrate (7.59 mmol, 0.37 mL) was added to a solution of 2-acetylcyclohexane-1,3-dione (7.59 mmol, 1.17 g) in EtOH (19 mL) at 0° C. and the reaction mixture was stirred at room temperature for 2 hours. After evaporation, the crude residue was purified by flash chromatography over silica gel using DCM/AcOEt (70:30 to 50:50) as eluent to yield 3-methyl-6,7-dihydro-1H-indazol-4(5H)-one (1.76 mmol, 265 mg, 23%) as a yellow solid.

UPLC-MS: RT=0.46 min; MS m/z ES$^+$=151.

5,5-Dibromo-3-methyl-6,7-dihydro-1H-indazol-4(5H)-one

According to Scheme 4 Step 4: Bromine (1.00 mmol, 51 μL) was added to a solution of 3-methyl-6,7-dihydro-1H-indazol-4(5H)-one (0.67 mmol, 100 mg) in CHCl$_3$ (3.3 mL) and the reaction mixture was stirred at room temperature for 12 hours. Bromine (1.00 mmol, 51 μL) was added and the reaction mixture was stirred at room temperature for 4 hours (Mixture of mono and dibrominated compounds). The reaction mixture was quenched with the addition of a solution of Na$_2$S$_2$O$_3$. The aqueous phase was extracted with DCM. The organic phase was washed with a saturated solution of NaHCO$_3$, was dried over Na$_2$SO$_4$ and concentrated to yield a mixture of 5,5-dibromo-3-methyl-6,7-dihydro-1H-indazol-4(5H)-one and of 5-bromo-3-methyl-6,7-dihydro-1H-indazol-4(5H)-one (37.5:62.5, 173 mg) as a brown oil.

UPLC-MS: RT=0.83 min; MS m/z ES$^+$=309.

8-Methyl-N-(pyridin-2-yl)-5,6-dihydro-4H-thiazolo[4,5-e]indazol-2-amine

According to Scheme 4 Step 5: A solution of a mixture of 5,5-dibromo-3-methyl-6,7-dihydro-1H-indazol-4(5H)one, 5-bromo-3-methyl-6,7-dihydro-1H-indazol-4(5H)-one (37.5:62.5, 173 mg) and of 1-(pyridin-2-yl)thiourea (0.67 mmol, 102 mg) in EtOH (2.4 mL) was stirred under reflux for 3 hours. The precipitate formed was filtered, was washed with a saturated solution of NaHCO$_3$, water, EtOH and Et$_2$O and was dried to yield 8-methyl-N-(pyridin-2-yl)-5,6-dihydro-4H-thiazolo[4,5-e]indazol-2-amine (46 μmol, 13 mg) as a white solid.

UPLC-MS: RT=0.70 min; MS m/z ES$^+$=284.

Example 6

2-Methyl-1-(2-(pyridin-2-ylamino)-4H-thiazolo[4,5-e]indazol-6(5H)-yl)propan-1-one (Final Compound 1-2)

According to Scheme 5: Isobutyryl chloride (0.37 mmol, 39 μL) was added dropwise to a solution of N-(pyridin-2-yl)-5,6-dihydro-4H-thiazolo[4,5-e]indazol-2-amine (0.37 mmol, 100 mg) in THF (2 mL) and the reaction mixture was stirred for 4 hours at room temperature. The reaction mixture was quenched with a saturated solution of NaHCO$_3$ and the aqueous phase was extracted with DCM. The organic phase was dried over Na$_2$SO$_4$, was filtered and was concentrated. The resulting crude product was purified by flash chromatography over silica gel using DCM as eluent to yield after evaporation 2-methyl-1-(2-(pyridin-2-ylamino)-4H-thiazolo[4,5-e]indazol-6(5H)-yl)propan-1-one (88 μmol, 30 mg, 23%) as a pale pink solid.

M.p.: 167-168° C.;

LC-MS: RT=2.75 min; MS m/z ES$^+$=340.

The compounds in the following Tables have been synthesised according to the same methods as previous examples 1 to 6, as denoted in the column denoted as "Exp. nr". The compounds denoted with the asterisk have been exemplified in the Examples.

TABLE 1

Compounds prepared according to the Examples.

| Co. nr. | Exp nr. | M | Y | |
|---|---|---|---|---|
| 1-1* | 1 | 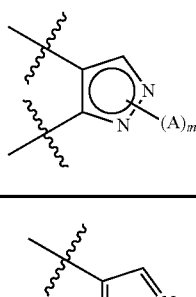 | —CH$_2$CH$_2$— | 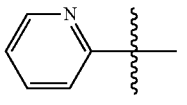 |
| 1-2* | 6 | 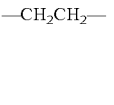 | —CH$_2$CH$_2$— | 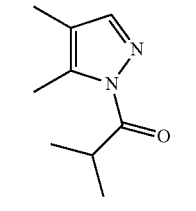 |
| 1-3* | 4 | 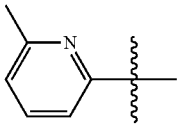 | —CH$_2$CH$_2$— | 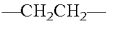 |
| 1-4 | 4 | 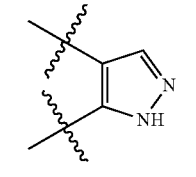 [SMILES: *c1cn[nH]c1*] | —CH$_2$CH$_2$— | 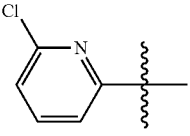 [SMILES: *c1cccc(Cl)n1] |

TABLE 1-continued
Compounds prepared according to the Examples.
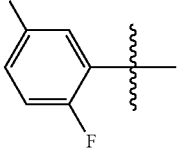
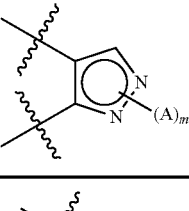
| Co. nr. | Exp nr. | M | Y | |
|---|---|---|---|---|
| 1-5 | 4 | 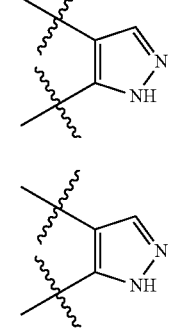 (2,5-difluorophenyl) | —CH$_2$CH$_2$— | 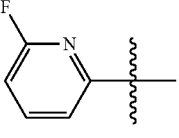 [SMILES: *c1cccc(F)n1] |
| 1-6 | 4 | 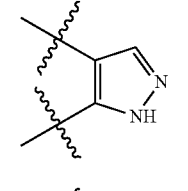 (6-fluoropyridin-2-yl) | —CH$_2$CH$_2$— | 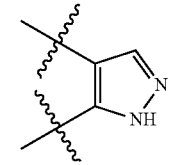 [SMILES: *c1cn[nH]c1*] |
| 1-7 | 1 | 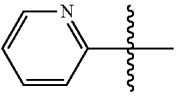 (pyridin-2-yl) | —CH(CH$_3$)CH$_2$— | 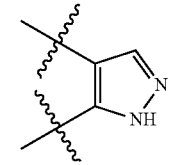 [SMILES: *c1cn[nH]c1*] |
| 1-8 | 1 | 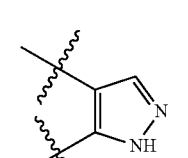 (pyridin-2-yl) | —CH$_2$CH$_2$CH$_2$— | 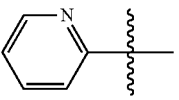 |
| 1-9 | 1 | 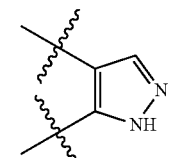 (pyridin-2-yl) | —CH(CH$_2$CH$_3$)CH$_2$— | 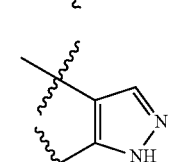 |
| 1-10 | 1 | 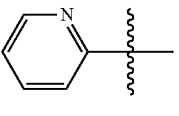 (3-fluoropyridin-2-yl) | —CH$_2$CH$_2$— | 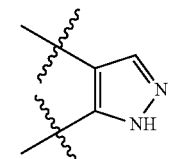 |
| 1-11 | 1 | 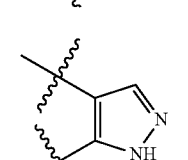 (6-methylpyridin-2-yl) | —CH$_2$CH$_2$CH$_2$— | 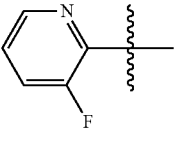 [SMILES: *c1ncccc1F] |

TABLE 1-continued

Compounds prepared according to the Examples.

| Co. nr. | Exp nr. | M | Y | (A)ₘ group |
|---|---|---|---|---|
| 1-12 | 1 | 5-F-pyridin-2-yl | —CH₂CH₂CH₂— | 1H-pyrazole |
| 1-13 | 1 | 3-F-pyridin-2-yl | —CH₂CH₂CH₂— | 1H-pyrazole |
| 1-14 | 1 | 6-MeO-pyridin-2-yl | —CH₂CH₂CH₂— | 1H-pyrazole |
| 1-15 | 1 | 5-F-pyridin-2-yl | —CH₂CH₂— | 1H-pyrazole |
| 1-16 | 1 | 6-Cl-pyridin-2-yl | —CH₂CH₂CH₂— | 1H-pyrazole |
| 1-17 | 1 | pyrazin-2-yl | —CH₂CH₂— | 1H-pyrazole |

TABLE 1-continued

Compounds prepared according to the Examples.

| Co. nr. | Exp nr. | M | Y | |
|---|---|---|---|---|
| 1-18 | 1 | cyclopentyl-CH< | —CH₂CH₂— | pyrazole-NH |
| 1-19* | 5 | pyridin-2-yl-CH< | —CH₂CH₂— | 3-methyl-pyrazole-NH |
| 1-20 | 1 | cyclobutyl-CH< | —CH₂CH₂— | pyrazole-NH |
| 1-21 | 1 | 6-fluoropyridin-2-yl-CH< | —CH₂CH₂CH₂— | pyrazole-NH |
| 1-22 | 1 | cyclopropyl-CH< | —CH₂CH₂CH₂— | pyrazole-NH |
| 1-23 | 1 | cyclobutyl-CH< | —CH₂CH₂CH₂— | pyrazole-NH |

TABLE 1-continued
Compounds prepared according to the Examples.
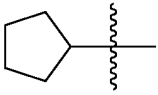 [SMILES: *C1CCCC1]
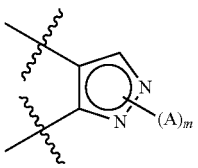
| Co. nr. | Exp nr. | M | Y | |
|---|---|---|---|---|
| 1-24 | 1 | 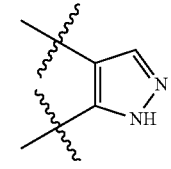 | —CH$_2$CH$_2$CH$_2$— | 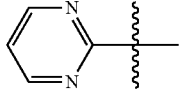 |
| 1-25 | 1 | 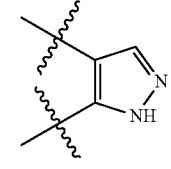 | —CH$_2$CH$_2$CH$_2$— | 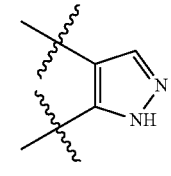 |
| 1-26 | 1 | 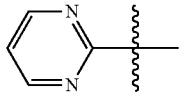 | —CH$_2$CH$_2$— | 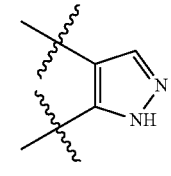 |
| 1-27 | 1 | 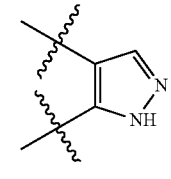 | —CH$_2$CH$_2$CH$_2$— | 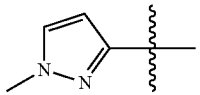 |
| 1-28 | 1 | 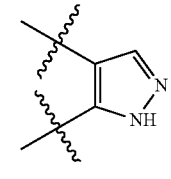 | —CH$_2$CH$_2$— | 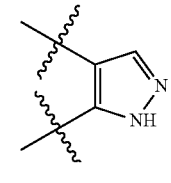 [SMILES: *c1cn[nH]c1*] |
| 1-29 | 1 | 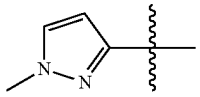 [SMILES: *c1ccn(C)n1] | —CH$_2$CH$_2$— | 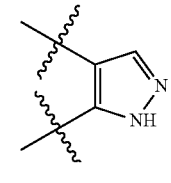 [SMILES: *c1cn[nH]c1*] |

TABLE 1-continued

Compounds prepared according to the Examples.

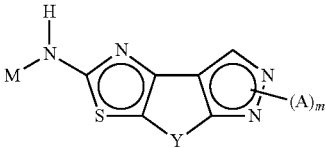

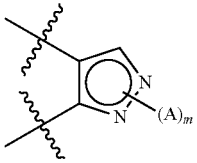

| Co. nr. | Exp nr. | M | Y | |
|---|---|---|---|---|
| 1-30 | 1 | 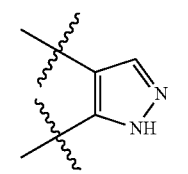 [SMILES: *c1cn[nH]c1*] | —CH$_2$CH$_2$CH$_2$— | 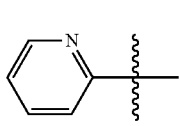 |
| 1-31 | 1 | 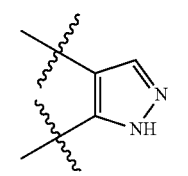 | —C(CH$_3$)$_2$CH$_2$— | 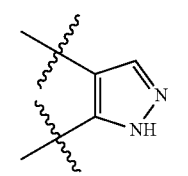 [SMILES: *c1cn[nH]c1*] |
| 1-32* | 2 | 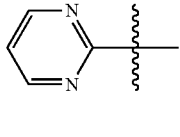 | —C(CH$_3$)$_2$CH$_2$— | 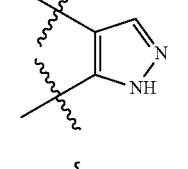 |
| 1-33 | 1 | 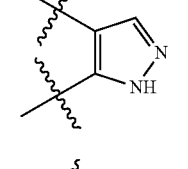 | —CH(CH$_3$)CH$_2$— | 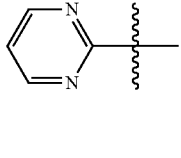 [SMILES: *c1ncccn1] |
| 1-34* | 3 | 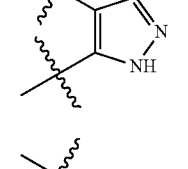 | —CH$_2$C(CH$_3$)$_2$— | 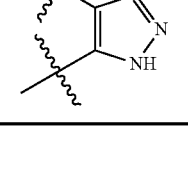 |

LC-MS and HPLC-MS methods:

Method 1

LC-MS were recorded on Waters Micromass ZQ 2996 system with the following conditions: Reversed phase HPLC was carried out on Zorbax SB-C18 cartridge (1.8 μm, 4.6×30 mm) from Agilent, with a flow rate of 1.5 mL/min. The gradient conditions used are: 90% A (water+0.1% of formic acid), 10% B (acetonitrile+0.1% of formic acid) to 100% B at 3.5 minutes, kept till 3.7 minutes and equilibrated to initial conditions at 3.8 minutes until 4.5 minutes. Injection volume 5-20 μL. ES MS detector was used, acquiring both in positive and negative ionization modes. Cone voltage was 30 V for both positive and negative ionization modes.

Method 2

UPLC-MS were recorded on Waters ACQUITY HPLC with the following conditions: Reversed phase HPLC was carried out on BEH-C18 cartridge (1.7 μm, 2.1×50 mm) from Waters, with a flow rate of 0.8 mL/min. The gradient conditions used are: 90% A (water+0.1% of formic acid), 10% B (acetonitrile+0.1% of formic acid) to 100% B at 1.3 minutes, kept till 1.6 minutes and equilibrated to initial conditions at 1.7 minutes until 2.0 minutes. Injection volume 5 μL. ES MS detector was used, acquiring both in positive and negative ionization modes.

All mass spectra were taken under electrospray ionisation (ESI) methods.

TABLE 2

Physico-chemical data for some compounds (nd = not determined).

| Co. Nr | Melting point (° C.) | MW (theor) | [MH+] | RT (min) | LCMS Method | Physical form |
|---|---|---|---|---|---|---|
| 1-1 | 297-299 | 269.32 | 270 | 0.60 | Method 2 | White solid |
| 1-2 | 167-168 | 339.41 | 340 | 2.75 | Method 1 | Pale pink solid |
| 1-3 | 280 (dec) | 283.35 | 284 | 1.71 | Method 1 | White solid |
| 1-4 | >300 | 303.77 | 304 | 2.12 | Method 1 | Pale pink solid |
| 1-5 | 270 (dec) | 304.32 | 305 | 2.17 | Method 1 | Beige solid |
| 1-6 | >300 | 287.32 | 288 | 1.96 | Method 1 | White solid |
| 1-7 | nd | 283.35 | 284 | 0.67 | Method 2 | Green solid |
| 1-8 | 279 (dec) | 283.35 | 284 | 0.63 | Method 2 | White solid |
| 1-9 | 317-319 | 297.38 | 298 | 0.74 | Method 2 | Beige solid |
| 1-10 | 300 (dec) | 287.32 | 288 | 0.75 | Method 2 | Brown solid |
| 1-11 | 312 (dec) | 297.38 | 298 | 0.65 | Method 2 | Beige solid |
| 1-12 | 314 (dec) | 301.34 | 302 | 0.82 | Method 2 | Beige solid |
| 1-13 | 300 (dec) | 301.34 | 302 | 0.89 | Method 2 | Brown solid |
| 1-14 | 300 (dec) | 313.38 | 314 | 0.91 | Method 2 | Brown solid |
| 1-15 | 315 (dec) | 287.31 | 288 | 0.82 | Method 2 | Yellow solid |
| 1-16 | 314 (dec) | 317.80 | 318 | 0.91 | Method 2 | Brown solid |
| 1-17 | >330 | 270.31 | 271 | 0.73 | Method 2 | Beige solid |
| 1-18 | 166-168 | 260.36 | 261 | 0.67 | Method 2 | Beige solid |
| 1-19 | nd | 283.35 | 284 | 0.70 | Method 2 | White solid |
| 1-20 | 144-146 | 246.33 | 247 | 0.65 | Method 2 | Yellow solid |
| 1-21 | 314 (dec) | 301.34 | 302 | 0.95 | Method 2 | Beige solid |
| 1-22 | 178-182 | 246.33 | 247 | 0.65 | Method 2 | White solid |
| 1-23 | 198-221 | 260.36 | 261 | 0.71 | Method 2 | White solid |
| 1-24 | 248 (dec) | 274.38 | 275 | 0.79 | Method 2 | White solid |
| 1-25 | 310 (dec) | 284.34 | 285 | 0.72 | Method 2 | White solid |
| 1-26 | 281-282 | 270.31 | 271 | 0.64 | Method 2 | White solid |
| 1-27 | 288-293 | 286.36 | 287 | 0.62 | Method 2 | Pink solid |
| 1-28 | nd | 272.33 | 273 | 0.56 | Method 2 | Brown solid |
| 1-29 | 283 (dec) | 284.34 | 285 | 1.79 | Method 1 | Brown solid |
| 1-30 | 297 (dec) | 298.37 | 299 | 0.71 | Method 2 | Brown solid |
| 1-31 | nd | 297.38 | 298 | 0.74 | Method 2 | Yellow solid |
| 1-32 | 298-306 | 298.37 | 299 | 0.75 | Method 2 | Yellow solid |
| 1-33 | >373 | 284.34 | 285 | 0.71 | Method 2 | Yellow solid |
| 1-34 | nd | 298.37 | 299 | 0.75 | Method 2 | Yellow solid |

Pharmacology

The compounds provided in the present invention are positive allosteric modulators of mGluR4. As such, these compounds do not appear to bind to the orthosteric glutamate recognition site, and do not activate the mGluR4 by themselves. Instead, the response of mGluR4 to a concentration of glutamate or mGluR4 agonist is increased when compounds of Formula I to III are present. Compounds of Formula I to III are expected to have their effect at mGluR4 by virtue of their ability to enhance the function of the receptor.

mGluR4 Assay on HEK-Expressing Human mGluR4

The compounds of the present invention are positive allosteric modulators of mGluR4 receptor. Their activity was examined on recombinant human mGluR4a receptors by detecting changes in intracellular $Ca^{2+}$ concentration, using the fluorescent $Ca^{2+}$-sensitive dye Fluo-4-(AM) and a Fluorometric Imaging Plate Reader (FLIPR, Molecular Devices, Sunnyvale, Calif.).

Transfection and Cell Culture

The cDNA encoding the human metabotropic glutamate receptor (hmGluR4), (accession number NM_000841.1, NCBI Nucleotide database browser), was subcloned into an expression vector containing also the hygromycin resistance gene. In parallel, the cDNA encoding a G protein allowing redirection of the activation signal to intracellular calcium flux was subcloned into a different expression vector containing also the puromycin resistance gene. Transfection of both these vectors into HEK293 cells with PolyFect reagent (Qiagen) according to supplier's protocol, and hygromycin and puromycin treatment allowed selection of antibiotic resistant cells which had integrated stably one or more copies of the plasmids. Positive cellular clones expressing hmGluR4 were identified in a functional assay measuring changes in calcium fluxes in response to glutamate or selective known mGluR4 orthosteric agonists and antagonists. HEK-293 cells expressing hmGluR4 were maintained in media containing DMEM, dialyzed Fetal Calf Serum (10%), Glutamax™ (2 mM), Penicillin (100 units/mL), Streptomycin (100 μg/mL), Geneticin (100 μg/mL) and Hygromycin-B (40 μg/mL) and puromycin (1 μg/mL) at 37° C./5% $CO_2$.

Fluorescent Cell Based-$Ca^{2+}$ Mobilization Assay

Human mGluR4HEK-293 cells were plated out 24 hours prior to FLIPR$^{384}$ assay in black-walled, clear-bottomed, poly-L-ornithine-coated 384-well plates at a density of 25,000 cells/well in a glutamine/glutamate free DMEM medium containing foetal bovine serum (10%), penicillin (100 units/mL) and streptomycin (100 μg/mL) at 37° C./5% $CO_2$.

On the day of the assay, the medium was aspirated and the cells were loaded with a 3 μM solution of Fluo-4-AM (LuBioScience, Lucerne, Switzerland) in 0.03% pluronic acid. After 1 hour at 37° C./5% $CO_2$, the non incorporated dye was removed by washing cell plate with the assay buffer and the cells were left in the dark at room temperature for six hours before testing. All assays were performed in a pH 7.4 buffered-solution containing 20 mM HEPES, 143 mM NaCl, 6 mM KCl, 1 mM $MgSO_4$, 1 mM $CaCl_2$, 0.125 mM sulfapyrazone and 0.1% glucose.

After 10 s of basal fluorescence recording, various concentrations of the compounds of the invention were added to the cells. Changes in fluorescence levels were first monitored for 180 s in order to detect any agonist activity of the compounds. Then the cells were stimulated by an $EC_{25}$ glutamate concentration for an additional 110 s in order to measure enhancing activities of the compounds of the invention. $EC_{25}$ glutamate concentration is the concentration giving 25% of the maximal glutamate response.

The concentration-response curves of representative compounds of the present invention were generated using the Prism GraphPad software (Graph Pad Inc, San Diego, USA). The curves were fitted to a four-parameter logistic equation:

$$Y = \text{Bottom} + (\text{Top} - \text{Bottom}) / (1 + 10^{((\text{LogEC}_{50} - X) * \text{Hill Slope})})$$

allowing the determination of $EC_{50}$ values.

The Table 3 below represents the mean $EC_{50}$ obtained from at least three independent experiments of selected molecules performed in duplicate.

TABLE 3

Activity data for selected compounds

| Compound no. | $Ca^{2+}$ Flux* |
|---|---|
| 1-1 | +++ |
| 1-3 | ++ |
| 1-5 | ++ |
| 1-6 | ++ |
| 1-8 | +++ |
| 1-13 | +++ |
| 1-14 | + |

*Table legend: + 1 μM < $EC_{50}$ < 10 μM ++ 100 nM < $EC_{50}$ < 1 μM +++ $EC_{50}$ < 100 nM The results shown in Table 3 demonstrate that the compounds described in the present invention are positive allosteric modulators of human mGluR4 receptors. These compounds do not have activity by themselves but they rather increase the functional activity and/or maximal efficacy of glutamate or mGluR4 agonist.

Thus, the positive allosteric modulators provided in the present invention are expected to increase the effectiveness of glutamate or mGluR4 agonists at mGluR4 receptor. Therefore, these positive allosteric modulators are expected to be useful for treatment of various neurological and psychiatric disorders associated with glutamate dysfunction described to be treated herein and others that can be treated by such positive allosteric modulators.

The compounds of the invention can be administered either alone, or in combination with other pharmaceutical agents effective in the treatment of conditions mentioned above.

Formulation Examples

Typical examples of recipes for the formulation of the invention are as follows:

1. Tablets

| | |
|---|---|
| Active ingredient | 5 to 50 mg |
| Di-calcium phosphate | 20 mg |
| Lactose | 30 mg |
| Talcum | 10 mg |
| Magnesium stearate | 5 mg |
| Potato starch | ad 200 mg |

In this Example, active ingredient can be replaced by the same amount of any of the compounds according to the present invention, in particular by the same amount of any of the exemplified compounds.

2. Suspension

An aqueous suspension is prepared for oral administration so that each 1 milliliter contains 1 to 5 mg of one of the active compounds, 50 mg of sodium carboxymethyl cellulose, 1 mg of sodium benzoate, 500 mg of sorbitol and water ad 1 mL.

3. Injectable

A parenteral composition is prepared by stirring 1.5% by weight of active ingredient of the invention in 10% by volume propylene glycol and water.

4. Ointment

| | |
|---|---|
| Active ingredient | 5 to 1000 mg |
| Stearyl alcohol | 3 g |
| Lanoline | 5 g |
| White petroleum | 15 g |
| Water | ad 100 g |

In this Example, active ingredient can be replaced with the same amount of any of the compounds according to the present invention, in particular by the same amount of any of the exemplified compounds.

Reasonable variations are not to be regarded as a departure from the scope of the invention. It will be obvious that the thus described invention may be varied in many ways by those skilled in the art.

The invention claimed is:

1. A compound having the Formula (I)

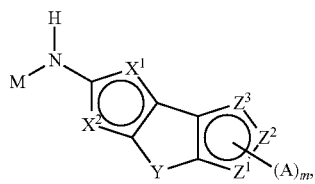

(I)

or a pharmaceutically acceptable acid or base addition salt thereof, a sterochemically isomeric form thereof or an N-oxide form thereof, wherein:

M is selected from a 3 to 10 membered ring selected from the group consisting of aryl, heteroaryl, heterocyclyl and cycloalkyl which can be substituted by a substituent selected from the group consisting of —$(C_1$-$C_6)$alkyl, halogen and —$(C_1$-$C_6)$alkyl-O—$(C_1$-$C_6)$alkyl;

$X^1$ is N;

$X^2$ is S;

Y is —$CR^4R^5$—$CR^6R^7$;

$Z^1$ is N; $Z^2$ is N; and $Z^3$ is C; representing a 5 membered heteroaryl ring which may further be substituted by 1 to 2 radicals $(A)_m$;

m is 1 or 2;

$(A)_m$ radicals are each independently selected from the group consisting of hydrogen, halogen, —CN, —OH, —$CF_3$, —SH, —$NH_2$ and a radical selected from the group consisting of —$(C_1$-$C_6)$alkyl, —$(C_1$-$C_6)$haloalkyl, —$(C_2$-$C_6)$alkynyl, —$(C_2$-$C_6)$alkenyl, —$(C_3$-$C_7)$cycloalkyl, —$(C_3$-$C_8)$cycloalkenyl, —$(C_1$-$C_6)$cyanoalkyl, —$(C_1$-$C_6)$alkylene-heteroaryl, —$(C_1$-$C_6)$alkylene-aryl, aryl, heteroaryl, heterocyclyl, —$(C_0$-$C_6)$alkyl-$OR^{10}$, —O—$(C_2$-$C_6)$alkylene-$OR^{10}$, —$NR^{10}(C_2$-$C_6)$alkylene-$OR^{11}$, —$(C_3$-$C_7)$cycloalkyl-$(C_1$-$C_6)$alkyl, —O—$(C_3$-$C_7)$cycloalkyl-$(C_1$-$C_6)$alkyl, —$NR^{10}$—$(C_3$-$C_7)$cycloalkyl-$(C_1$-$C_6)$alkyl, —$(C_1$-$C_6)$haloalkyl-$OR^{10}$, —$(C_1$-$C_6)$haloalkyl-$NR^{10}R^{11}$, —$(C_3$-$C_6)$alkynyl-$OR^{10}$, —$(C_3$-$C_6)$alkynyl-$NR^{10}R^{11}$, —$(C_3$-$C_6)$alkenyl-$OR^{10}$, —$(C_3$-$C_6)$alkenyl -$NR^{10}R^{11}$, —$(C_0$-$C_6)$alkyl-S—$R^{10}$, —O—$(C_2$-$C_6)$alkylene-S—$R^{10}$, —$NR^{10}$—$(C_2$-$C_6)$alkylene-S—$R^{11}$, —$(C_0$-$C_6)$alkyl-S(=O)—$R^{10}$, —O—$(C_1$-$C_6)$alkylene-S(=O)—$R^{10}$, —$NR^{10}$—$(C_1$-$C_6)$alkylene-S(=O)—$R^{11}$, —$(C_0$-$C_6)$alkyl-S(=O)$_2$-$R^{10}$, —O—$(C_1$-$C_6)$alkylene-S(=O)$_2$—$R^{10}$, —$NR^{10}$—$(C_1$-$C_6)$alkylene-S(=O)$_2$—$R^{11}$, —$(C_0$-$C_6)$alkyl-$NR^{10}R^{11}$, —O—$(C_2$-$C_6)$alkylene-$NR^{10}R^{11}$, —$NR^{10}$—$(C_2$-$C_6)$alkylene-$NR^{11}R^{12}$, —$(C_0$-$C_6)$alkyl-S(=O)$_2$$NR^{10}R^{11}$, —O—$(C_1$-$C_6)$alkylene-S(=O)$_2$$NR^{10}R^{11}$, —$NR^{10}$—$(C_1$-$C_6)$alkylene -S(=O)$_2$$NR^{11}R^{12}$, —$(C_0$-$C_6)$alkyl-$NR^{10}$—S(=O)$_2$$R^{11}$, —O—$(C_2$-$C_6)$alkylene-$NR^{10}$—S(=O)$_2$$R^{11}$, —$NR^{10}$—$(C_2$-$C_6)$alkylene-$NR^{11}$—S(=O)$_2$$R^{12}$, —$(C_0$-$C_6)$alkyl-C(=O)—$NR^{10}R^{11}$, —O—$(C_1$-$C_6)$alkylene -C(=O)—$NR^{10}R^{11}$, —$NR^{10}$—$(C_1$-$C_6)$alkylene-C(=O)—$NR^{11}R^{12}$, —$(C_0$-$C_6)$alkyl-$NR^{10}C(=O)$—$R^{11}$, —O—$(C_2$-$C_6)$alkylene-$NR^{10}C(=O)$—$R^{11}$, —$NR^{10}$—$(C_2$-$C_6)$alkylene-$NR^{11}C(=O)$—$R^{12}$, —$(C_0$-$C_6)$alkyl -OC(=O)—$R^{10}$, —O—$(C_2$-$C_6)$alkylene-OC(=O)—$R^{10}$, —$NR^{10}$—$(C_2$-$C_6)$alkylene-OC(=O)—$R^{11}$, —$(C_0$-$C_6)$alkyl-C(=O)—$OR^{10}$, —O—$(C_1$-$C_6)$alkylene-C(=O)—$OR^{10}$, —$NR^{10}$—$(C_1$-$C_6)$alkylene-C(=O)—$OR^{11}$, —$(C_0$-$C_6)$alkyl-C(=O)—$R^{10}$, —O—$(C_1$-$C_6)$alkylene-C(=O)—$R^{10}$, —$NR^{10}$—$(C_1$-$C_6)$alkylene -C(=O)—$R^{11}$, —$(C_0$-$C_6)$alkyl-$NR^{10}$—C(=O)—$OR^{11}$, —$(C_0$-$C_6)$alkyl-O—C(=O)—$NR^{10}R^{11}$, —$(C_0$-$C_6)$alkyl-$NR^{10}$—C(=$NR^{11}$)—$NR^{12}R^{13}$, —$(C_0$-$C_6)$alkyl-$NR^{10}$-C(=O)—$NR^{11}R^{12}$, —O—$(C_2$-$C_6)$alkylene-$NR^{10}$—C(=O)—$NR^{11}R^{12}$, —$NR^{10}$—$(C_2$-$C_6)$alkylene-$NR^{11}$—C(=O)—$NR^{12}R^{13}$ and —$(C_0$-$C_6)$alkyl-$NR^{10}$—C(=S)—$NR^{11}R^{12}$;

$R^1$, $R^2$, $R^3$, $R^4$, $R^5$, $R^6$, $R^7$, $R^8$, $R^9$, $R^{10}$, $R^{11}$, $R^{12}$ and $R^{13}$ are each independently selected from the group consisting of hydrogen and a radical selected from the group consisting of —$(C_1$-$C_6)$haloalkyl, —$(C_1$-$C_6)$alkyl, —$(C_1$-$C_6)$cyanoalkyl, —$(C_3$-$C_7)$cycloalkyl, —$(C_4$-$C_{10})$alkylene-cycloalkyl, heteroaryl, —$(C_1$-$C_6)$alkylene-heteroaryl, aryl, heterocyclyl and —$(C_1$-$C_6)$alkylene-aryl.

2. A compound according to claim 1 having the Formula (II)

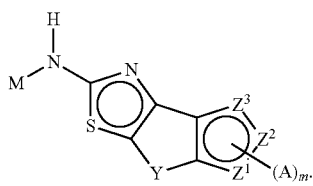

(II)

or a pharmaceutically acceptable acid or base addition salt thereof, a sterochemically isomeric form thereof or an N-oxide form thereof, wherein:
M is selected from a 3 to 10 membered ring selected from the group consisting of aryl, heteroaryl, heterocyclyl and cycloalkyl which can be substituted by a substituent selected from the group consisting of —$(C_1$-$C_6)$alkyl, halogen and —$(C_1$-$C_6)$alkyl-O—$(C_1$-$C_6)$alkyl;
m is 1;
$(A)_m$ radicals are each independently selected from the group consisting of hydrogen, halogen and a radical selected from the group consisting of —$(C_1$-$C_6)$alkyl and —$(C_0$-$C_6)$alkyl -C(=O)—$R^{10}$;
$R^{10}$, $R^{11}$ and $R^{12}$ are each independently selected from the group consisting of hydrogen and a radical selected from the group consisting of —$(C_1$-$C_6)$haloalkyl, —$(C_1$-$C_6)$ alkyl, —$(C_1$-$C_6)$cyanoalkyl, —$(C_3$-$C_7)$cycloalkyl, —$(C_4$-$C_{10})$alkylene-cycloalkyl, heteroaryl, —$(C_1$-$C_6)$ alkylene-heteroaryl, aryl, heterocyclyl and —$(C_1$-$C_6)$ alkylene-aryl.

3. A compound according to claim 2 having the Formula (III)

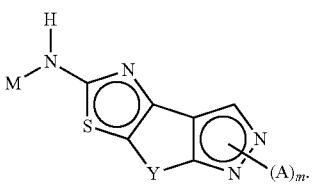

(III)

or a pharmaceutically acceptable acid or base addition salt thereof, a sterochemically isomeric form thereof or an N-oxide form thereof, wherein:
M is selected from a 3 to 10 membered ring selected from the group consisting of aryl, heteroaryl, heterocyclyl and cycloalkyl which can be substituted by a substituent selected from the group consisting of —$(C_1$-$C_6)$alkyl, halogen and —$(C_1$-$C_6)$alkyl-O—$(C_1$-$C_6)$alkyl;
m is 1;
$(A)_m$ radicals are each independently selected from the group consisting of hydrogen and a radical selected from the group consisting of —$(C_1$-$C_6)$alkyl and —$(C_0$-$C_6)$ alkyl-C(=O)—$R^{10}$;
$R^{10}$ is selected from the group consisting of hydrogen and a radical selected from the group consisting of —$(C_1$-$C_6)$haloalkyl, —$(C_1$-$C_6)$alkyl, —$(C_1$-$C_6)$cyanoalkyl, —$(C_3$-$C_7)$cycloalkyl, —$(C_4$-$C_{10})$alkylene-cycloalkyl, heteroaryl, —$(C_1$-$C_6)$alkylene-heteroaryl, aryl, heterocyclyl and -$C_1$-$C_6)$alkylene-aryl.

4. A compound as in any of claims 1-3, which can exist as optical isomers, wherein said compound is either the racemic mixture or one or both of the individual optical isomers.

5. A compound according to claim 1, wherein:
M is selected from a 3 to 10 membered ring selected from the group consisting of aryl, heteroaryl, heterocyclyl and cycloalkyl which can be substituted by a substituent selected from the group consisting of —$(C_1$-$C_6)$alkyl, halogen and —$(C_1$-$C_6)$alkyl-O—$(C_1$-$C_6)$alkyl;
m is 1;
$(A)_m$ radicals are each independently selected from the group consisting of hydrogen, —CN, —OH, —$CF_3$, —SH and a radical selected from the group consisting of —$(C_1$-$C_6)$alkyl, —$(C_0$-$C_6)$alkyl-C(=O)—$R^{10}$ and —$NR^{10}$—$(C_2$-$C_6)$alkylene-OC(=O)—$R^{11}$;
$R^{10}$ and $R^{11}$ are each independently selected from the group consisting of hydrogen and a radical selected from the group consisting of —$(C_1$-$C_6)$haloalkyl, —$(C_1$-$C_6)$ alkyl, —$(C_1$-$C_6)$cyanoalkyl, —$(C_3$-$C_7)$cycloalkyl, —$(C_4$-$C_{10})$alkylene-cycloalkyl, heteroaryl, —$(C_1$-$C_6)$ alkylene-heteroaryl, aryl, heterocyclyl and —$(C_1$-$C_6)$ alkylene-aryl.

6. A compound according to claim 1, wherein said compound is selected from:
N-(Pyridin-2-yl)-5,6-dihydro-4H-thiazolo[4,5-e]indazol-2-amine;
2-Methyl-1-(2-(pyridin-2-ylamino)-4H-thiazolo[4,5-e]indazol-6(5H)-yl)propan-1-one;
N-(6-Methylpyridin-2-yl)-5,6-dihydro-4H-thiazolo[4,5-e]indazol-2-amine;
N-(6-Chloropyridin-2-yl)-5,6-dihydro-4H-thiazolo[4,5-e]indazol-2-amine;
N-(2,5-Difluorophenyl)-5,6-dihydro-4H-thiazolo[4,5-e]indazol-2-amine;
N-(6-Fluoropyridin-2-yl)-5,6-dihydro-4H-thiazolo[4,5-e]indazol-2-amine;
4-Methyl-N-(pyridin-2-yl)-5,6-dihydro-4H-thiazolo[4,5-e]indazol-2-amine;
4-Ethyl-N-(pyridin-2-yl)-5,6-dihydro-4H-thiazolo[4,5-e]indazol-2-amine
N-(3-Fluoropyridin-2-yl)-5,6-dihydro-4H-thiazolo[4,5-e]indazol-2-amine;
N-(5-Fluoropyridin-2-yl)-5,6-dihydro-4H-thiazolo[4,5-e]indazol-2-amine;
N-(Pyrazin-2-yl)-5,6-dihydro-4H-thiazolo[4,5-e]indazol-2-amine;
N-Cyclopentyl-5,6-dihydro-4H-thiazolo[4,5-e]indazol-2-amine;
8-Methyl-N-(pyridin-2-yl)-5,6-dihydro-4H-thiazolo[4,5-e]indazol-2-amine;
N-(Pyrimdin-2yl)-5,6-dihydro-4H-thiazolo[4,5-e]indazol-2-amine;
N-(1-Methyl-1H-pyrazol-3-yl)-5,6-dihydro-4H-thiazolo[4,5-e]indazol-2-amine; and
N-(4-Methylpyrimidin-2-yl)-5,6-dihydro-4H-thiazolo[4,5-e]indazol-2-amine
or a pharmaceutically acceptable acid or base addition salt thereof, a stereochemically isomeric form thereof and an N-oxide form thereof.

7. A compound according to any of claims 1, wherein said compound is selected from:
4,4-Dimethyl-N-(pyridin-2-yl)-5,6-dihydro-4H-thiazolo[4,5-e]indazol-2-amine;
4,4-Dimethyl-N-(pyrimidin-2-yl)-5,6-dihydro-4H-thiazolo[4,5-e]indazol-2-amine;
4-Methyl-N-(pyrimidin-2-yl)-5,6-dihydro-4H-thiazolo[4,5-e]indazol-2-amine;
5,5-Dimethyl-N-(pyrimidin-2-yl)-5,6-dihydro-4H-thiazolo[4,5-e]indazol-2-amine or a pharmaceutically acceptable acid or base addition salt thereof, a stereochemically isomeric form thereof and an N-oxide form thereof.

8. A pharmaceutical composition comprising a therapeutically effective amount of a compound according to claim 1 and pharmaceutically acceptable carrier and/or excipient.

9. A method of modulating mGluR4 activity in a mammal comprising administering to said mammal a therapeutically effective amount of a compound according to claim 1.

10. A method according to claim 9, wherein said mammal is a human.

11. A method of modulating mGluR4 activity in a mammal comprising administering to a said mammal a therapeutically effective amount of a pharmaceutical composition according to claim 8.

12. A method according to claim 11, wherein said mammal is a human.

* * * * *